United States Patent [19]

Buckholz

[11] Patent Number: 5,268,273
[45] Date of Patent: Dec. 7, 1993

[54] PICHIA PASTORIS ACID PHOSPHATASE GENE, GENE REGIONS, SIGNAL SEQUENCE AND EXPRESSION VECTORS COMPRISING SAME

[75] Inventor: Richard G. Buckholz, Encinitas, Calif.

[73] Assignee: Phillips Petroleum Company, Bartlesville, Okla.

[21] Appl. No.: 627,539

[22] Filed: Dec. 14, 1990

[51] Int. Cl.$^5$ .................. C12N 15/55; C12N 1/19; C12N 15/81; C12P 21/02
[52] U.S. Cl. .................. 435/69.1; 435/69.9; 435/196; 435/215; 435/254.23; 435/19; 435/320.1; 435/938; 536/23.74; 536/24.1; 935/10; 935/28; 935/37; 935/69
[58] Field of Search ................ 536/27, 23.74, 24.1; 435/69.1, 69.9, 193, 196, 215, 255, 320.1, 19, 938; 935/10, 28, 37, 69

[56] References Cited

U.S. PATENT DOCUMENTS

| | | | |
|---|---|---|---|
| 4,753,879 | 6/1988 | Rosa et al. | 435/172.3 |
| 4,808,537 | 2/1989 | Stroman et al. | 435/6 |
| 4,855,231 | 8/1989 | Stroman et al. | 435/68 |
| 4,876,197 | 10/1989 | Burke et al. | 432/172.3 |
| 4,882,279 | 11/1989 | Cregg et al. | 435/172.3 |
| 4,885,242 | 12/1989 | Cregg et al. | 435/68 |
| 4,895,800 | 1/1990 | Tschoff et al. | 435/69.3 |
| 5,002,876 | 3/1991 | Sreekrishna et al. | 435/69.5 |
| 5,102,789 | 4/1992 | Siegel et al. | 435/69.9 |
| 5,132,404 | 7/1992 | Ohtani et al. | 530/362 |

FOREIGN PATENT DOCUMENTS 0178105 4/1986 European Pat. Off.
228080 7/1987 European Pat. Off.
0288435 10/1988 European Pat. Off.

OTHER PUBLICATIONS

Hollander, "Acid Phosphatases", pp. 449-498 in *The Enzymes*, ed. Paul Boyer, 1971, vol. IV.
Tait-Kamradt et al., *Molecular and Cellular Biology* 6: 1855-1865, Jun. 1986.
Digan et al., *Developments in Industrial Microbiology* 29: 59-65, 1988.
Lemontt et al., *DNA* 4: 419-428, 1985.
Ausubel et al., Editors, *Current Protocols in Molecular Biology*, pp. 3.0.1-3.0.2, 1988.
Proc. Natl. Acad. Sci. U.S.A., vol. 78, (No. 7), pp. 4510-4514 (1981).

Primary Examiner—Robert A. Wax
Assistant Examiner—Stephen Walsh
Attorney, Agent, or Firm—Fitch, Even, Tabin & Flannery

[57] ABSTRACT

The present invention discloses the *Pichia pastoris* acid phospbatase gene, which includes the 5' regulatory region, signal sequence, structural gene, and 3' transcription termination sequence. Also disclosed are methods of using these fragments, which include but are not limited to the secretion of proteins from cells and the regulation of the transcription of DNA. DNA vectors containing the acid phospbatase gene or fragments thereof and hosts transformed with these vectors are also disclosed. Additionally, integrative vectors which direct integration at the *Pichia pastoris* PHO1 locus and a method of identifying these disruptants is disclosed.

44 Claims, 1 Drawing Sheet

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 1993 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 400..1803

( x i ) SEQUENCE DESCRIPTION: SEQ ID NO:1:

```
GGATCCCTAT TGTTACTTTT GCTTAACATT CCAATATTCT TCAACGGTTA ATTGATTAAC      60

ACTGTAACCT CTGCCCATGT GCTTCATCCA AATCTGGTAA TCTGCTTTCT ATTTCTGCCA     120

AAATAGTTAA TCTATGAGAC ATGTGCCCTC AATTGCGCAG TAGATCGAGT GGAAGTCTTC     180

TTTGCGTAAC ACTCAAAGTA TATCCCTGTT AGTCTTTATT CACCTGTTGC TGCATTGGTG     240

TCAGTTACCA TTATTGTTTC CACTTGGAAA AGCTTGTTTT TTTTGATAG  CACAGAAACG     300

TGGGCTCCGA TAAGCTAAAC TTCAACGAGA ATATAAAGC  TGAAAAGATT CTTGTCAAGA     360

ACTTGTACAA CGACCAATAA GTCTTTCAAG GCATCAGAC ATG TTT TCT CCT ATT        414
                                             Met Phe Ser Pro Ile
                                             1               5
```

| | | | | | | | | | | | | | | | | |
|---|---|---|---|---|---|---|---|---|---|---|---|---|---|---|---|---|
| CTA | AGT | CTG | GAA | ATT | ATT | CTC | GCT | TTG | GCT | ACT | CTC | CAA | TCA | GTC | TTT | 462 |
| Leu | Ser | Leu | Glu | Ile | Ile | Leu | Ala | Leu | Ala | Thr | Leu | Gln | Ser | Val | Phe | |
| | | | | 10 | | | | | 15 | | | | | 20 | | |
| GCG | GTT | GAG | TTG | CAG | CAC | GTT | CTT | GGA | GTC | AAC | GAC | AGA | CCC | TAT | CCT | 510 |
| Ala | Val | Glu | Leu | Gln | His | Val | Leu | Gly | Val | Asn | Asp | Arg | Pro | Tyr | Pro | |
| | | | 25 | | | | | 30 | | | | | 35 | | | |
| CAG | AGG | ACA | GAT | GAT | CAG | TAC | AAC | ATT | CTG | AGA | CAT | CTG | GGA | GGC | TTG | 558 |
| Gln | Arg | Thr | Asp | Asp | Gln | Tyr | Asn | Ile | Leu | Arg | His | Leu | Gly | Gly | Leu | |
| | | 40 | | | | | 45 | | | | | 50 | | | | |
| GGC | CCC | TAC | ATC | GGT | TAC | AAT | GGA | TGG | GGA | ATT | GCT | GCT | GAG | TCT | GAA | 606 |
| Gly | Pro | Tyr | Ile | Gly | Tyr | Asn | Gly | Trp | Gly | Ile | Ala | Ala | Glu | Ser | Glu | |
| | 55 | | | | | 60 | | | | | 65 | | | | | |
| ATT | GAA | TCC | TGT | ACG | ATT | GAT | CAG | GCT | CAT | CTG | TTG | ATG | AGA | CAT | GGA | 654 |
| Ile | Glu | Ser | Cys | Thr | Ile | Asp | Gln | Ala | His | Leu | Leu | Met | Arg | His | Gly | |
| 70 | | | | | 75 | | | | | 80 | | | | | 85 | |
| GAA | AGA | TAC | CCA | AGT | ACC | AAT | GTG | GGG | AAA | CAA | CTA | GAA | GCT | TTG | TAC | 702 |
| Glu | Arg | Tyr | Pro | Ser | Thr | Asn | Val | Gly | Lys | Gln | Leu | Glu | Ala | Leu | Tyr | |
| | | | | 90 | | | | | 95 | | | | | 100 | | |
| CAG | AAA | CTA | CTA | GAT | GCT | GAT | GTG | GAA | GTC | CCT | ACA | GGA | CCA | TTG | TCT | 750 |
| Gln | Lys | Leu | Leu | Asp | Ala | Asp | Val | Glu | Val | Pro | Thr | Gly | Pro | Leu | Ser | |
| | | | 105 | | | | | 110 | | | | | 115 | | | |
| TTC | TTT | CAA | GAC | TAT | GAT | TAC | TTC | GTC | TCT | GAC | GCC | GCT | TGG | TAC | GAG | 798 |
| Phe | Phe | Gln | Asp | Tyr | Asp | Tyr | Phe | Val | Ser | Asp | Ala | Ala | Trp | Tyr | Glu | |
| | | 120 | | | | | 125 | | | | | 130 | | | | |
| CAA | GAA | ACA | ACT | AAG | GGT | TTC | TAC | TCG | GGG | TTA | AAC | ACC | GCT | TTC | GAT | 846 |
| Gln | Glu | Thr | Thr | Lys | Gly | Phe | Tyr | Ser | Gly | Leu | Asn | Thr | Ala | Phe | Asp | |
| | 135 | | | | | 140 | | | | | 145 | | | | | |
| TTT | GGT | ACC | ACT | TTG | AGA | GAA | CGA | TAT | GAA | CAT | TTG | ATA | AAC | AAT | AGC | 894 |
| Phe | Gly | Thr | Thr | Leu | Arg | Glu | Arg | Tyr | Glu | His | Leu | Ile | Asn | Asn | Ser | |
| 150 | | | | | 155 | | | | | 160 | | | | | 165 | |
| GAA | GAA | GGA | AAG | AAA | CTT | TCT | GTT | TGG | GCT | GGC | TCT | CAA | GAA | AGA | GTT | 942 |
| Glu | Glu | Gly | Lys | Lys | Leu | Ser | Val | Trp | Ala | Gly | Ser | Gln | Glu | Arg | Val | |
| | | | | 170 | | | | | 175 | | | | | 180 | | |
| GTT | GAC | AAC | GCA | AAG | TAC | TTT | GCT | CAA | GGA | TTT | ATG | AAA | TCT | AAC | TAC | 990 |
| Val | Asp | Asn | Ala | Lys | Tyr | Phe | Ala | Gln | Gly | Phe | Met | Lys | Ser | Asn | Tyr | |
| | | | 185 | | | | | 190 | | | | | 195 | | | |
| ACC | GTT | ATG | GTC | GAA | GTC | GTT | GCT | CTA | GAA | GAG | GAG | AAA | TCC | CAG | GGA | 1038 |
| Thr | Val | Met | Val | Glu | Val | Val | Ala | Leu | Glu | Glu | Glu | Lys | Ser | Gln | Gly | |
| | | 200 | | | | | 205 | | | | | 210 | | | | |
| CTC | AAC | TCT | CTA | ACG | GCT | CGA | ATT | TCA | TGT | CCA | AAC | TAT | AAC | AGC | CAT | 1086 |
| Leu | Asn | Ser | Leu | Thr | Ala | Arg | Ile | Ser | Cys | Pro | Asn | Tyr | Asn | Ser | His | |
| | 215 | | | | | 220 | | | | | 225 | | | | | |
| ATC | TAC | AAA | GAT | GGC | GAC | TTG | GGG | AAT | GAC | ATT | GCT | CAA | AGA | GAA | GCT | 1134 |
| Ile | Tyr | Lys | Asp | Gly | Asp | Leu | Gly | Asn | Asp | Ile | Ala | Gln | Arg | Glu | Ala | |
| 230 | | | | | 235 | | | | | 240 | | | | | 245 | |
| GAC | AGA | TTG | AAC | ACT | CTT | TCT | CCA | GGA | TTT | AAC | ATT | ACT | GCA | GAT | GAT | 1182 |
| Asp | Arg | Leu | Asn | Thr | Leu | Ser | Pro | Gly | Phe | Asn | Ile | Thr | Ala | Asp | Asp | |
| | | | | 250 | | | | | 255 | | | | | 260 | | |
| ATT | CCA | ACA | ATT | GCC | CTA | TAC | TGT | GGC | TTT | GAA | CTA | AAT | GTA | AGA | GGT | 1230 |
| Ile | Pro | Thr | Ile | Ala | Leu | Tyr | Cys | Gly | Phe | Glu | Leu | Asn | Val | Arg | Gly | |
| | | | 265 | | | | | 270 | | | | | 275 | | | |
| GAG | TCA | TCC | TTC | TGT | GAC | GTC | TTG | TCA | AGA | GAG | GCT | CTA | CTG | TAC | ACT | 1278 |
| Glu | Ser | Ser | Phe | Cys | Asp | Val | Leu | Ser | Arg | Glu | Ala | Leu | Leu | Tyr | Thr | |
| | | 280 | | | | | 285 | | | | | 290 | | | | |
| GCT | TAT | CTT | AGA | GAT | TTG | GGA | TGG | TAT | TAC | AAT | GTT | GGA | AAC | GGG | AAC | 1326 |
| Ala | Tyr | Leu | Arg | Asp | Leu | Gly | Trp | Tyr | Tyr | Asn | Val | Gly | Asn | Gly | Asn | |
| | 295 | | | | | 300 | | | | | 305 | | | | | |
| CCA | CTT | GGA | AAG | ACA | ATC | GGC | TAC | GTC | TAT | GCC | AAC | GCC | ACA | AGA | CAG | 1374 |
| Pro | Leu | Gly | Lys | Thr | Ile | Gly | Tyr | Val | Tyr | Ala | Asn | Ala | Thr | Arg | Gln | |
| 310 | | | | | 315 | | | | | 320 | | | | | 325 | |
| CTG | TTG | GAA | AAC | ACA | GAA | GCT | GAT | CCT | AGA | GAT | TAT | CCT | TTG | TAC | TTT | 1422 |

-continued

```
Leu Leu Glu Asn Thr Glu Ala Asp Pro Arg Asp Tyr Pro Leu Tyr Phe
            330                 335                 340

TCC TTT AGT CAT GAT ACC GAT CTG CTT CAA GTA TTC ACT TCA CTC GGT    1470
Ser Phe Ser His Asp Thr Asp Leu Leu Gln Val Phe Thr Ser Leu Gly
            345                 350                 355

CTT TTC AAC GTG ACA GAT CTG CCA TTA GAC CAG ATT CAA TTC CAG ACC    1518
Leu Phe Asn Val Thr Asp Leu Pro Leu Asp Gln Ile Gln Phe Gln Thr
            360                 365                 370

TCT TTC AAA TCT ACC GAA ATA GTT CCC ATG GGA GCA AGA TTG CTT ACC    1566
Ser Phe Lys Ser Thr Glu Ile Val Pro Met Gly Ala Arg Leu Leu Thr
    375                 380                 385

GAG AGA TTA TTG TGT ACT GTT GAA GGT GAA GAA AAA TAC TAC GTT AGA    1614
Glu Arg Leu Leu Cys Thr Val Glu Gly Glu Glu Lys Tyr Tyr Val Arg
390                 395                 400                 405

ACT ATC CTC AAC GAT GCA GTC TTC CCA CTG AGT GAC TGT TCC TCT GGC    1662
Thr Ile Leu Asn Asp Ala Val Phe Pro Leu Ser Asp Cys Ser Ser Gly
                410                 415                 420

CCT GGA TTC TCT TGT CCG TTG AAC GAT TAT GTT TCT AGA CTT GAG GCA    1710
Pro Gly Phe Ser Cys Pro Leu Asn Asp Tyr Val Ser Arg Leu Glu Ala
            425                 430                 435

TTG AAC GAG GAC AGT GAC TTT GCG GAA AAC TGT GGA GTT CCT AAA AAT    1758
Leu Asn Glu Asp Ser Asp Phe Ala Glu Asn Cys Gly Val Pro Lys Asn
        440                 445                 450

GCT TCC TAC CCA CTT GAA CTA TCA TTC TTC TGG GAT GAC TTG TCA        1803
Ala Ser Tyr Pro Leu Glu Leu Ser Phe Phe Trp Asp Asp Leu Ser
    455                 460                 465

TAAAAATGGT AAGGAATGTT TTGCATCAGA TACGAGTTCA AAACGATTAA GAAGAGAATG  1863

CTCTTTTTTT TGTTTCTATC CAATTGGACT ATTTTCGTTT ATTTTAAATA GCGTACAACT  1923

TTAACTAGAT GATATCTTCT TCTTCAAACG ATACCACTTC TCTCATACTA GGTGGAGGTT  1983

CAATGGATCC                                                          1993
```

( 2 ) INFORMATION FOR SEQ ID NO:2:

( i ) SEQUENCE CHARACTERISTICS:
        ( A ) LENGTH: 468 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Phe Ser Pro Ile Leu Ser Leu Glu Ile Ile Leu Ala Leu Ala Thr
1               5                   10                  15

Leu Gln Ser Val Phe Ala Val Glu Leu Gln His Val Leu Gly Val Asn
            20                  25                  30

Asp Arg Pro Tyr Pro Gln Arg Thr Asp Asp Gln Tyr Asn Ile Leu Arg
        35                  40                  45

His Leu Gly Gly Leu Gly Pro Tyr Ile Gly Tyr Asn Gly Trp Gly Ile
    50                  55                  60

Ala Ala Glu Ser Glu Ile Glu Ser Cys Thr Ile Asp Gln Ala His Leu
65                  70                  75                  80

Leu Met Arg His Gly Glu Arg Tyr Pro Ser Thr Asn Val Gly Lys Gln
            85                  90                  95

Leu Glu Ala Leu Tyr Gln Lys Leu Leu Asp Ala Asp Val Glu Val Pro
            100                 105                 110

Thr Gly Pro Leu Ser Phe Phe Gln Asp Tyr Asp Tyr Phe Val Ser Asp
        115                 120                 125

Ala Ala Trp Tyr Glu Gln Glu Thr Thr Lys Gly Phe Tyr Ser Gly Leu
    130                 135                 140
```

| | | | | | | | | | | | | | | | |
|---|---|---|---|---|---|---|---|---|---|---|---|---|---|---|---|
|Asn|Thr|Ala|Phe|Asp|Phe|Gly|Thr|Thr|Leu|Arg|Glu|Arg|Tyr|Glu|His|
|145| | | | |150| | | |155| | | | |160| |

| | | | | | | | | | | | | | | | |
|---|---|---|---|---|---|---|---|---|---|---|---|---|---|---|---|
|Leu|Ile|Asn|Asn|Ser|Glu|Glu|Gly|Lys|Lys|Leu|Ser|Val|Trp|Ala|Gly|
| | | | |165| | | |170| | | | |175| | |

| | | | | | | | | | | | | | | | |
|---|---|---|---|---|---|---|---|---|---|---|---|---|---|---|---|
|Ser|Gln|Glu|Arg|Val|Val|Asp|Asn|Ala|Lys|Tyr|Phe|Ala|Gln|Gly|Phe|
| | | |180| | | | |185| | | | |190| | |

| | | | | | | | | | | | | | | | |
|---|---|---|---|---|---|---|---|---|---|---|---|---|---|---|---|
|Met|Lys|Ser|Asn|Tyr|Thr|Val|Met|Val|Glu|Val|Val|Ala|Leu|Glu|Glu|
| | |195| | | | |200| | | | |205| | | |

| | | | | | | | | | | | | | | | |
|---|---|---|---|---|---|---|---|---|---|---|---|---|---|---|---|
|Glu|Lys|Ser|Gln|Gly|Leu|Asn|Ser|Leu|Thr|Ala|Arg|Ile|Ser|Cys|Pro|
| |210| | | | |215| | | | |220| | | | |

| | | | | | | | | | | | | | | | |
|---|---|---|---|---|---|---|---|---|---|---|---|---|---|---|---|
|Asn|Tyr|Asn|Ser|His|Ile|Tyr|Lys|Asp|Gly|Asp|Leu|Gly|Asn|Asp|Ile|
|225| | | | |230| | | |235| | | | | |240|

| | | | | | | | | | | | | | | | |
|---|---|---|---|---|---|---|---|---|---|---|---|---|---|---|---|
|Ala|Gln|Arg|Glu|Ala|Asp|Arg|Leu|Asn|Thr|Leu|Ser|Pro|Gly|Phe|Asn|
| | | | |245| | | | |250| | | | |255| |

| | | | | | | | | | | | | | | | |
|---|---|---|---|---|---|---|---|---|---|---|---|---|---|---|---|
|Ile|Thr|Ala|Asp|Asp|Ile|Pro|Thr|Ile|Ala|Leu|Tyr|Cys|Gly|Phe|Glu|
| | | |260| | | | |265| | | | |270| | |

| | | | | | | | | | | | | | | | |
|---|---|---|---|---|---|---|---|---|---|---|---|---|---|---|---|
|Leu|Asn|Val|Arg|Gly|Glu|Ser|Ser|Phe|Cys|Asp|Val|Leu|Ser|Arg|Glu|
| | |275| | | | |280| | | | |285| | | |

| | | | | | | | | | | | | | | | |
|---|---|---|---|---|---|---|---|---|---|---|---|---|---|---|---|
|Ala|Leu|Leu|Tyr|Thr|Ala|Tyr|Leu|Arg|Asp|Leu|Gly|Trp|Tyr|Tyr|Asn|
| |290| | | | |295| | | | |300| | | | |

| | | | | | | | | | | | | | | | |
|---|---|---|---|---|---|---|---|---|---|---|---|---|---|---|---|
|Val|Gly|Asn|Gly|Asn|Pro|Leu|Gly|Lys|Thr|Ile|Gly|Tyr|Val|Tyr|Ala|
|305| | | | |310| | | |315| | | | | |320|

| | | | | | | | | | | | | | | | |
|---|---|---|---|---|---|---|---|---|---|---|---|---|---|---|---|
|Asn|Ala|Thr|Arg|Gln|Leu|Leu|Glu|Asn|Thr|Glu|Ala|Asp|Pro|Arg|Asp|
| | | |325| | | | |330| | | | |335| | |

| | | | | | | | | | | | | | | | |
|---|---|---|---|---|---|---|---|---|---|---|---|---|---|---|---|
|Tyr|Pro|Leu|Tyr|Phe|Ser|Phe|Ser|His|Asp|Thr|Asp|Leu|Leu|Gln|Val|
| | | |340| | | | |345| | | | |350| | |

| | | | | | | | | | | | | | | | |
|---|---|---|---|---|---|---|---|---|---|---|---|---|---|---|---|
|Phe|Thr|Ser|Leu|Gly|Leu|Phe|Asn|Val|Thr|Asp|Leu|Pro|Leu|Asp|Gln|
| | |355| | | | |360| | | | |365| | | |

| | | | | | | | | | | | | | | | |
|---|---|---|---|---|---|---|---|---|---|---|---|---|---|---|---|
|Ile|Gln|Phe|Gln|Thr|Ser|Phe|Lys|Ser|Thr|Glu|Ile|Val|Pro|Met|Gly|
| |370| | | | |375| | | | |380| | | | |

| | | | | | | | | | | | | | | | |
|---|---|---|---|---|---|---|---|---|---|---|---|---|---|---|---|
|Ala|Arg|Leu|Leu|Thr|Glu|Arg|Leu|Leu|Cys|Thr|Val|Glu|Gly|Glu|Glu|
|385| | | | |390| | | | |395| | | | |400|

| | | | | | | | | | | | | | | | |
|---|---|---|---|---|---|---|---|---|---|---|---|---|---|---|---|
|Lys|Tyr|Tyr|Val|Arg|Thr|Ile|Leu|Asn|Asp|Ala|Val|Phe|Pro|Leu|Ser|
| | | | |405| | | | |410| | | | |415| |

| | | | | | | | | | | | | | | | |
|---|---|---|---|---|---|---|---|---|---|---|---|---|---|---|---|
|Asp|Cys|Ser|Ser|Gly|Pro|Gly|Phe|Ser|Cys|Pro|Leu|Asn|Asp|Tyr|Val|
| | | |420| | | | |425| | | | |430| | |

| | | | | | | | | | | | | | | | |
|---|---|---|---|---|---|---|---|---|---|---|---|---|---|---|---|
|Ser|Arg|Leu|Glu|Ala|Leu|Asn|Glu|Asp|Ser|Asp|Phe|Ala|Glu|Asn|Cys|
| | |435| | | | |440| | | | |445| | | |

| | | | | | | | | | | | | | | | |
|---|---|---|---|---|---|---|---|---|---|---|---|---|---|---|---|
|Gly|Val|Pro|Lys|Asn|Ala|Ser|Tyr|Pro|Leu|Glu|Leu|Ser|Phe|Phe|Trp|
|450| | | | |455| | | | |460| | | | | |

| | | | |
|---|---|---|---|
|Asp|Asp|Leu|Ser|
|465| | | |

( 2 ) INFORMATION FOR SEQ ID NO:3:

( i ) SEQUENCE CHARACTERISTICS:
        ( A ) LENGTH: 399 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:3:

```
GGATCCCTAT TGTTACTTTT GCTTAACATT CCAATATTCT TCAACGGTTA ATTGATTAAC    60
ACTGTAACCT CTGCCCATGT GCTTCATCCA AATCTGGTAA TCTGCTTTCT ATTTCTGCCA   120
AAATAGTTAA TCTATGAGAC ATGTGCCCTC AATTGCGCAG TAGATCGAGT GGAAGTCTTC   180
```

```
TTTGCGTAAC ACTCAAAGTA TATCCCTGTT AGTCTTTATT CACCTGTTGC TGCATTGGTG    240

TCAGTTACCA TTATTGTTTC CACTTGGAAA AGCTTGTTTT TTTTTGATAG CACAGAAACG    300

TGGGCTCCGA TAAGCTAAAC TTCAACGAGA ATATAAAAGC TGAAAAGATT CTTGTCAAGA    360

ACTTGTACAA CGACCAATAA GTCTTTCAAG GCATCAGAC                           399
```

( 2 ) INFORMATION FOR SEQ ID NO:4:

( i ) SEQUENCE CHARACTERISTICS:
        ( A ) LENGTH: 66 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..66

( x i ) SEQUENCE DESCRIPTION: SEQ ID NO:4:

```
ATG TTT TCT CCT ATT CTA AGT CTG GAA ATT ATT CTC GCT TTG GCT ACT     48
Met Phe Ser Pro Ile Leu Ser Leu Glu Ile Ile Leu Ala Leu Ala Thr
 1               5                  10                  15

CTC CAA TCA GTC TTT GCG                                             66
Leu Gln Ser Val Phe Ala
            20
```

( 2 ) INFORMATION FOR SEQ ID NO:5:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Phe Ser Pro Ile Leu Ser Leu Glu Ile Ile Leu Ala Leu Ala Thr
 1               5                  10                  15

Leu Gln Ser Val Phe Ala
            20
```

( 2 ) INFORMATION FOR SEQ ID NO:6:

( i ) SEQUENCE CHARACTERISTICS:
        ( A ) LENGTH: 1341 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..1338

( x i ) SEQUENCE DESCRIPTION: SEQ ID NO:6:

```
GTT GAG TTG CAG CAC GTT CTT GGA GTC AAC GAC AGA CCC TAT CCT CAG     48
Val Glu Leu Gln His Val Leu Gly Val Asn Asp Arg Pro Tyr Pro Gln
 1               5                  10                  15

AGG ACA GAT GAT CAG TAC AAC ATT CTG AGA CAT CTG GGA GGC TTG GGC     96
Arg Thr Asp Asp Gln Tyr Asn Ile Leu Arg His Leu Gly Gly Leu Gly
            20                  25                  30

CCC TAC ATC GGT TAC AAT GGA TGG GGA ATT GCT GCT GAG TCT GAA ATT    144
Pro Tyr Ile Gly Tyr Asn Gly Trp Gly Ile Ala Ala Glu Ser Glu Ile
        35                  40                  45

GAA TCC TGT ACG ATT GAT CAG GCT CAT CTG TTG ATG AGA CAT GGA GAA    192
Glu Ser Cys Thr Ile Asp Gln Ala His Leu Leu Met Arg His Gly Glu
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| AGA | TAC | CCA | AGT | ACC | AAT | GTG | GGG | AAA | CAA | CTA | GAA | GCT | TTG | TAC | CAG | 240  |
| Arg | Tyr | Pro | Ser | Thr | Asn | Val | Gly | Lys | Gln | Leu | Glu | Ala | Leu | Tyr | Gln |      |
| 65  |     |     |     | 70  |     |     |     |     | 75  |     |     |     |     |     | 80  |      |
| AAA | CTA | CTA | GAT | GCT | GAT | GTG | GAA | GTC | CCT | ACA | GGA | CCA | TTG | TCT | TTC | 288  |
| Lys | Leu | Leu | Asp | Ala | Asp | Val | Glu | Val | Pro | Thr | Gly | Pro | Leu | Ser | Phe |      |
|     |     |     |     | 85  |     |     |     |     | 90  |     |     |     |     | 95  |     |      |
| TTT | CAA | GAC | TAT | GAT | TAC | TTC | GTC | TCT | GAC | GCC | GCT | TGG | TAC | GAG | CAA | 336  |
| Phe | Gln | Asp | Tyr | Asp | Tyr | Phe | Val | Ser | Asp | Ala | Ala | Trp | Tyr | Glu | Gln |      |
|     |     |     | 100 |     |     |     |     | 105 |     |     |     |     | 110 |     |     |      |
| GAA | ACA | ACT | AAG | GGT | TTC | TAC | TCG | GGG | TTA | AAC | ACC | GCT | TTC | GAT | TTT | 384  |
| Glu | Thr | Thr | Lys | Gly | Phe | Tyr | Ser | Gly | Leu | Asn | Thr | Ala | Phe | Asp | Phe |      |
|     |     |     | 115 |     |     |     |     | 120 |     |     |     |     | 125 |     |     |      |
| GGT | ACC | ACT | TTG | AGA | GAA | CGA | TAT | GAA | CAT | TTG | ATA | AAC | AAT | AGC | GAA | 432  |
| Gly | Thr | Thr | Leu | Arg | Glu | Arg | Tyr | Glu | His | Leu | Ile | Asn | Asn | Ser | Glu |      |
|     |     |     | 130 |     |     |     |     | 135 |     |     |     |     | 140 |     |     |      |
| GAA | GGA | AAG | AAA | CTT | TCT | GTT | TGG | GCT | GGC | TCT | CAA | GAA | AGA | GTT | GTT | 480  |
| Glu | Gly | Lys | Lys | Leu | Ser | Val | Trp | Ala | Gly | Ser | Gln | Glu | Arg | Val | Val |      |
| 145 |     |     |     |     | 150 |     |     |     |     | 155 |     |     |     |     | 160 |      |
| GAC | AAC | GCA | AAG | TAC | TTT | GCT | CAA | GGA | TTT | ATG | AAA | TCT | AAC | TAC | ACC | 528  |
| Asp | Asn | Ala | Lys | Tyr | Phe | Ala | Gln | Gly | Phe | Met | Lys | Ser | Asn | Tyr | Thr |      |
|     |     |     |     | 165 |     |     |     |     | 170 |     |     |     |     | 175 |     |      |
| GTT | ATG | GTC | GAA | GTC | GTT | GCT | CTA | GAA | GAG | GAG | AAA | TCC | CAG | GGA | CTC | 576  |
| Val | Met | Val | Glu | Val | Val | Ala | Leu | Glu | Glu | Glu | Lys | Ser | Gln | Gly | Leu |      |
|     |     |     |     | 180 |     |     |     |     | 185 |     |     |     |     | 190 |     |      |
| AAC | TCT | CTA | ACG | GCT | CGA | ATT | TCA | TGT | CCA | AAC | TAT | AAC | AGC | CAT | ATC | 624  |
| Asn | Ser | Leu | Thr | Ala | Arg | Ile | Ser | Cys | Pro | Asn | Tyr | Asn | Ser | His | Ile |      |
|     |     |     | 195 |     |     |     |     | 200 |     |     |     |     | 205 |     |     |      |
| TAC | AAA | GAT | GGC | GAC | TTG | GGG | AAT | GAC | ATT | GCT | CAA | AGA | GAA | GCT | GAC | 672  |
| Tyr | Lys | Asp | Gly | Asp | Leu | Gly | Asn | Asp | Ile | Ala | Gln | Arg | Glu | Ala | Asp |      |
|     |     |     | 210 |     |     |     |     | 215 |     |     |     |     | 220 |     |     |      |
| AGA | TTG | AAC | ACT | CTT | TCT | CCA | GGA | TTT | AAC | ATT | ACT | GCA | GAT | GAT | ATT | 720  |
| Arg | Leu | Asn | Thr | Leu | Ser | Pro | Gly | Phe | Asn | Ile | Thr | Ala | Asp | Asp | Ile |      |
| 225 |     |     |     |     | 230 |     |     |     |     | 235 |     |     |     |     | 240 |      |
| CCA | ACA | ATT | GCC | CTA | TAC | TGT | GGC | TTT | GAA | CTA | AAT | GTA | AGA | GGT | GAG | 768  |
| Pro | Thr | Ile | Ala | Leu | Tyr | Cys | Gly | Phe | Glu | Leu | Asn | Val | Arg | Gly | Glu |      |
|     |     |     |     | 245 |     |     |     |     | 250 |     |     |     |     | 255 |     |      |
| TCA | TCC | TTC | TGT | GAC | GTC | TTG | TCA | AGA | GAG | GCT | CTA | CTG | TAC | ACT | GCT | 816  |
| Ser | Ser | Phe | Cys | Asp | Val | Leu | Ser | Arg | Glu | Ala | Leu | Leu | Tyr | Thr | Ala |      |
|     |     |     | 260 |     |     |     |     | 265 |     |     |     |     | 270 |     |     |      |
| TAT | CTT | AGA | GAT | TTG | GGA | TGG | TAT | TAC | AAT | GTT | GGA | AAC | GGG | AAC | CCA | 864  |
| Tyr | Leu | Arg | Asp | Leu | Gly | Trp | Tyr | Tyr | Asn | Val | Gly | Asn | Gly | Asn | Pro |      |
|     |     | 275 |     |     |     |     | 280 |     |     |     |     | 285 |     |     |     |      |
| CTT | GGA | AAG | ACA | ATC | GGC | TAC | GTC | TAT | GCC | AAC | GCC | ACA | AGA | CAG | CTG | 912  |
| Leu | Gly | Lys | Thr | Ile | Gly | Tyr | Val | Tyr | Ala | Asn | Ala | Thr | Arg | Gln | Leu |      |
| 290 |     |     |     |     | 295 |     |     |     |     | 300 |     |     |     |     |     |      |
| TTG | GAA | AAC | ACA | GAA | GCT | GAT | CCT | AGA | GAT | TAT | CCT | TTG | TAC | TTT | TCC | 960  |
| Leu | Glu | Asn | Thr | Glu | Ala | Asp | Pro | Arg | Asp | Tyr | Pro | Leu | Tyr | Phe | Ser |      |
| 305 |     |     |     |     | 310 |     |     |     |     | 315 |     |     |     |     | 320 |      |
| TTT | AGT | CAT | GAT | ACC | GAT | CTG | CTT | CAA | GTA | TTC | ACT | TCA | CTC | GGT | CTT | 1008 |
| Phe | Ser | His | Asp | Thr | Asp | Leu | Leu | Gln | Val | Phe | Thr | Ser | Leu | Gly | Leu |      |
|     |     |     |     | 325 |     |     |     |     | 330 |     |     |     |     | 335 |     |      |
| TTC | AAC | GTG | ACA | GAT | CTG | CCA | TTA | GAC | CAG | ATT | CAA | TTC | CAG | ACC | TCT | 1056 |
| Phe | Asn | Val | Thr | Asp | Leu | Pro | Leu | Asp | Gln | Ile | Gln | Phe | Gln | Thr | Ser |      |
|     |     |     | 340 |     |     |     |     | 345 |     |     |     |     | 350 |     |     |      |
| TTC | AAA | TCT | ACC | GAA | ATA | GTT | CCC | ATG | GGA | GCA | AGA | TTG | CTT | ACC | GAG | 1104 |
| Phe | Lys | Ser | Thr | Glu | Ile | Val | Pro | Met | Gly | Ala | Arg | Leu | Leu | Thr | Glu |      |
|     |     | 355 |     |     |     |     | 360 |     |     |     |     | 365 |     |     |     |      |
| AGA | TTA | TTG | TGT | ACT | GTT | GAA | GGT | GAA | GAA | AAA | TAC | TAC | GTT | AGA | ACT | 1152 |
| Arg | Leu | Leu | Cys | Thr | Val | Glu | Gly | Glu | Glu | Lys | Tyr | Tyr | Val | Arg | Thr |      |
| 370 |     |     |     |     | 375 |     |     |     |     | 380 |     |     |     |     |     |      |

| | | | | | | | | | | | | | | | | |
|---|---|---|---|---|---|---|---|---|---|---|---|---|---|---|---|---|
|ATC|CTC|AAC|GAT|GCA|GTC|TTC|CCA|CTG|AGT|GAC|TGT|TCC|TCT|GGC|CCT|1200|
|Ile|Leu|Asn|Asp|Ala|Val|Phe|Pro|Leu|Ser|Asp|Cys|Ser|Ser|Gly|Pro| |
|385| | | | |390| | | |395| | | | |400| | |

| | | | | | | | | | | | | | | | | |
|---|---|---|---|---|---|---|---|---|---|---|---|---|---|---|---|---|
|GGA|TTC|TCT|TGT|CCG|TTG|AAC|GAT|TAT|GTT|TCT|AGA|CTT|GAG|GCA|TTG|1248|
|Gly|Phe|Ser|Cys|Pro|Leu|Asn|Asp|Tyr|Val|Ser|Arg|Leu|Glu|Ala|Leu| |
| | | | |405| | | |410| | | |415| | | | |

| | | | | | | | | | | | | | | | | |
|---|---|---|---|---|---|---|---|---|---|---|---|---|---|---|---|---|
|AAC|GAG|GAC|AGT|GAC|TTT|GCG|GAA|AAC|TGT|GGA|GTT|CCT|AAA|AAT|GCT|1296|
|Asn|Glu|Asp|Ser|Asp|Phe|Ala|Glu|Asn|Cys|Gly|Val|Pro|Lys|Asn|Ala| |
| | | |420| | | | |425| | | |430| | | | |

| | | | | | | | | | | | | |
|---|---|---|---|---|---|---|---|---|---|---|---|---|
|TCC|TAC|CCA|CTT|GAA|CTA|TCA|TTC|TTC|TGG|GAT|GAC|TTG|TCA|1338|
|Ser|Tyr|Pro|Leu|Glu|Leu|Ser|Phe|Phe|Trp|Asp|Asp|Leu|Ser| |
| | |435| | | |440| | | | |445| | | |

TAA      1341

( 2 ) INFORMATION FOR SEQ ID NO:7:

( i ) SEQUENCE CHARACTERISTICS:
        ( A ) LENGTH: 446 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| | | | | | | | | | | | | | | |
|---|---|---|---|---|---|---|---|---|---|---|---|---|---|---|
|Val|Glu|Leu|Gln|His|Val|Leu|Gly|Val|Asn|Asp|Arg|Pro|Tyr|Pro|Gln|
|1| | | |5| | | | |10| | | | |15|
|Arg|Thr|Asp|Asp|Gln|Tyr|Asn|Ile|Leu|Arg|His|Leu|Gly|Gly|Leu|Gly|
| | | |20| | | | |25| | | | |30| | |
|Pro|Tyr|Ile|Gly|Tyr|Asn|Gly|Trp|Gly|Ile|Ala|Ala|Glu|Ser|Glu|Ile|
| | | |35| | | | |40| | | | |45| | |
|Glu|Ser|Cys|Thr|Ile|Asp|Gln|Ala|His|Leu|Leu|Met|Arg|His|Gly|Glu|
| |50| | | | |55| | | | |60| | | | |
|Arg|Tyr|Pro|Ser|Thr|Asn|Val|Gly|Lys|Gln|Leu|Glu|Ala|Leu|Tyr|Gln|
|65| | | | |70| | | | |75| | | | |80|
|Lys|Leu|Leu|Asp|Ala|Asp|Val|Glu|Val|Pro|Thr|Gly|Pro|Leu|Ser|Phe|
| | | | |85| | | | |90| | | | |95| |
|Phe|Gln|Asp|Tyr|Asp|Tyr|Phe|Val|Ser|Asp|Ala|Ala|Trp|Tyr|Glu|Gln|
| | | |100| | | | |105| | | | |110| | |
|Glu|Thr|Thr|Lys|Gly|Phe|Tyr|Ser|Gly|Leu|Asn|Thr|Ala|Phe|Asp|Phe|
| | | |115| | | | |120| | | | |125| | |
|Gly|Thr|Thr|Leu|Arg|Glu|Arg|Tyr|Glu|His|Leu|Ile|Asn|Asn|Ser|Glu|
| |130| | | | |135| | | | |140| | | | |
|Glu|Gly|Lys|Lys|Leu|Ser|Val|Trp|Ala|Gly|Ser|Gln|Glu|Arg|Val|Val|
|145| | | | |150| | | | |155| | | | |160|
|Asp|Asn|Ala|Lys|Tyr|Phe|Ala|Gln|Gly|Phe|Met|Lys|Ser|Asn|Tyr|Thr|
| | | | |165| | | | |170| | | | |175| |
|Val|Met|Val|Glu|Val|Val|Ala|Leu|Glu|Glu|Lys|Ser|Gln|Gly|Leu|
| | | |180| | | | |185| | | | |190| | |
|Asn|Ser|Leu|Thr|Ala|Arg|Ile|Ser|Cys|Pro|Asn|Tyr|Asn|Ser|His|Ile|
| | |195| | | | |200| | | | |205| | | |
|Tyr|Lys|Asp|Gly|Asp|Leu|Gly|Asn|Asp|Ile|Ala|Gln|Arg|Glu|Ala|Asp|
| |210| | | | |215| | | | |220| | | | |
|Arg|Leu|Asn|Thr|Leu|Ser|Pro|Gly|Phe|Asn|Ile|Thr|Ala|Asp|Asp|Ile|
|225| | | | |230| | | | |235| | | | |240|
|Pro|Thr|Ile|Ala|Leu|Tyr|Cys|Gly|Phe|Glu|Leu|Asn|Val|Arg|Gly|Glu|
| | | | |245| | | | |250| | | | |255| |
|Ser|Ser|Phe|Cys|Asp|Val|Leu|Ser|Arg|Glu|Ala|Leu|Leu|Tyr|Thr|Ala|
| | | |260| | | | |265| | | | |270| | |
|Tyr|Leu|Arg|Asp|Leu|Gly|Trp|Tyr|Tyr|Asn|Val|Gly|Asn|Gly|Asn|Pro|

|   | 275 |   |   |   | 280 |   |   |   |   | 285 |   |   |   |
|---|---|---|---|---|---|---|---|---|---|---|---|---|---|

Leu Gly Lys Thr Ile Gly Tyr Val Tyr Ala Asn Ala Thr Arg Gln Leu
    290                            295                            300

Leu Glu Asn Thr Glu Ala Asp Pro Arg Asp Tyr Pro Leu Tyr Phe Ser
305                          310                        315                      320

Phe Ser His Asp Thr Asp Leu Leu Gln Val Phe Thr Ser Leu Gly Leu
                    325                        330                        335

Phe Asn Val Thr Asp Leu Pro Leu Asp Gln Ile Gln Phe Gln Thr Ser
                  340                      345                    350

Phe Lys Ser Thr Glu Ile Val Pro Met Gly Ala Arg Leu Leu Thr Glu
        355                      360                        365

Arg Leu Leu Cys Thr Val Glu Gly Glu Glu Lys Tyr Tyr Val Arg Thr
    370                      375                        380

Ile Leu Asn Asp Ala Val Phe Pro Leu Ser Asp Cys Ser Ser Gly Pro
385                    390                      395                  400

Gly Phe Ser Cys Pro Leu Asn Asp Tyr Val Ser Arg Leu Glu Ala Leu
                  405                      410                  415

Asn Glu Asp Ser Asp Phe Ala Glu Asn Cys Gly Val Pro Lys Asn Ala
            420                      425                  430

Ser Tyr Pro Leu Glu Leu Ser Phe Phe Trp Asp Asp Leu Ser
        435                    440                  445

( 2 ) INFORMATION FOR SEQ ID NO:8:

( i ) SEQUENCE CHARACTERISTICS:
        ( A ) LENGTH: 187 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:8:

AAATGGTAAG GAATGTTTTG CATCAGATAC GAGTTCAAAA CGATTAAGAA GAGAATGCTC   60

TTTTTTTTGT TTCTATCCAA TTGGACTATT TTCGTTTATT TTAAATAGCG TACAACTTTA  120

ACTAGATGAT ATCTTCTTCT TCAAACGATA CCACTTCTCT CATACTAGGT GGAGGTTCAA  180

TGGATCC   187

( 2 ) INFORMATION FOR SEQ ID NO:9:

( i ) SEQUENCE CHARACTERISTICS:
        ( A ) LENGTH: 109 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:9:

CTAGATGGAT GCAATGAAGA GAGGGCTCTG CTGTGTGCTG CTGCTGTGTG GAGCAGTCTT   60

CGTTTCGCCC AGCCAGGAAA TCCATGCCCG ATTCAGAAGA GGAGCCAGA   109

( 2 ) INFORMATION FOR SEQ ID NO:10:

( i ) SEQUENCE CHARACTERISTICS:
        ( A ) LENGTH: 33 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:10:

CTGGCTGGGC GAAACGAAGA CTGCTCCACA CAG                                        33

(2) INFORMATION FOR SEQ ID NO:11:

(i) SEQUENCE CHARACTERISTICS:
          (A) LENGTH: 37 base pairs
          (B) TYPE: nucleic acid
          (C) STRANDEDNESS: unknown
          (D) TOPOLOGY: unknown (ii) MOLECULE TYPE: DNA (genomic)

(xi) SEQUENCE DESCRIPTION: SEQ ID NO:11:

CTAGTCTGGC TCCTCTTCTG AATCGGGCAT GGATTTC                                    37

(2) INFORMATION FOR SEQ ID NO:12:

(i) SEQUENCE CHARACTERISTICS:
          (A) LENGTH: 39 base pairs
          (B) TYPE: nucleic acid
          (C) STRANDEDNESS: unknown
          (D) TOPOLOGY: unknown (ii) MOLECULE TYPE: DNA (genomic)

(xi) SEQUENCE DESCRIPTION: SEQ ID NO:12:

CAGCAGCACA CAGCAGAGCC CTCTCTTCAT TGCATCCAT                                  39

(2) INFORMATION FOR SEQ ID NO:13:

(i) SEQUENCE CHARACTERISTICS:
          (A) LENGTH: 37 base pairs
          (B) TYPE: nucleic acid
          (C) STRANDEDNESS: unknown
          (D) TOPOLOGY: unknown (ii) MOLECULE TYPE: DNA (genomic)

(xi) SEQUENCE DESCRIPTION: SEQ ID NO:13:

GATTCAGAGG AGCCAGATCT TACCAAGTGA TCTGCAG                                    37

(2) INFORMATION FOR SEQ ID NO:14:

(i) SEQUENCE CHARACTERISTICS:
          (A) LENGTH: 37 base pairs
          (B) TYPE: nucleic acid
          (C) STRANDEDNESS: unknown
          (D) TOPOLOGY: unknown (ii) MOLECULE TYPE: DNA (genomic)

(xi) SEQUENCE DESCRIPTION: SEQ ID NO:14:

ACTAATTATT CGAAACGATG GATGCAATGA AGAGAGG                                    37

(2) INFORMATION FOR SEQ ID NO:15:

(i) SEQUENCE CHARACTERISTICS:
          (A) LENGTH: 28 base pairs
          (B) TYPE: nucleic acid
          (C) STRANDEDNESS: unknown
          (D) TOPOLOGY: unknown (ii) MOLECULE TYPE: DNA (genomic)

(xi) SEQUENCE DESCRIPTION: SEQ ID NO:15:

CGAGGAATTC CCCGGGATCC TTAGACAT                                              28

(2) INFORMATION FOR SEQ ID NO:16:

(i) SEQUENCE CHARACTERISTICS:

(A) LENGTH: 53 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:16:

AATTCATGTT CTCTCCAATT TTGTCCTTGG AAATTATTTT AGCTTTGGCT ACT  53

(2) INFORMATION FOR SEQ ID NO:17:

(i) SEQUENCE CHARACTERISTICS:
(A) LENGTH: 49 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:17:

AGTAGCCAAA GCTAAAATAA TTTCCAAGGA CAAAATTGGA GAGAACATG  49

(2) INFORMATION FOR SEQ ID NO:18:

(i) SEQUENCE CHARACTERISTICS:
(A) LENGTH: 22 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:18:

TTGCAATCTG TCTTCGCTCG AG  22

(2) INFORMATION FOR SEQ ID NO:19:

(i) SEQUENCE CHARACTERISTICS:
(A) LENGTH: 26 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:19:

AATTCTCGAG CGAAGACAGA TTGCAA  26

(2) INFORMATION FOR SEQ ID NO:20:

(i) SEQUENCE CHARACTERISTICS:
(A) LENGTH: 31 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:20:

CTAATTATTC GAAACGATGT TCTCTCCAAT T  31

PICHIA PASTORIS ACID PHOSPHATASE GENE, GENE REGIONS, SIGNAL SEQUENCE AND EXPRESSION VECTORS COMPRISING SAME

FIELD OF THE INVENTION

This invention relates to the field of recombinant biotechnology utilizing yeast host systems and expression vectors. In one aspect the invention relates to novel DNA fragments containing part or all of the yeast *Pichia pastoris* acid pbosphatase gene (SEQ ID NO:1). In another aspect the invention relates to novel vectors containing DNA fragments derived from the *Pichia pastoris* acid phosphatase gene (SEQ ID NO:1). In yet another aspect the invention relates to host cells transformed with vectors coiitaiiiing fragments derived from the *Pichia pastoris* acid phosphatase gene (SEQ ID NO:1). In another aspect the invention relates to using the above-described DNA fragments to facilitate the expression and/or secretion of beterologous proteins in yeast.

BACKGROUND OF THE INVENTION

As recombinant DNA biotechnology has developed in recent years, the controlled production by microorganisms of an enormous variety of useful polypeptides has become possible. Many polypeptides, such as for example human growth hormone, leukocyte interferons, human insulin, and human proinsulin liave already been produced by various microorganisms. The continued application of techniques already in hand is expected to permit production of a variety of other useful polypeptide products.

The basic techniques employed in the field of recombinant DNA technology are known by those of skill in the art. The elements desirably present for the practice of recombinant DNA technology include but are not limited to:

(1) a gene coding for one or more desired polypeptide(s) and functionally associated with adequate control sequences required for expression of the gene in the bost organism;
(2) a vector into which the gene can be inserted;
(3) a suitable bost organism into which the vector carrying the gene can be transformed;
(4) if secretion of the heterologous protein is desired, a signal sequence capable of directing the heterologous protein into the secretion pathway of the host cell, and thereafter out of the cell;
(5) a transformation system; and
(6) a method of selecting transformants.

Recombinant gene constructs can be designed such that the recombinant protein transits the host's secretory pathway and is secreted into the growth media. Secretion is a desired mode of recombinant expression for several reasons. First, some heterologous proteins have a toxic effect on ttie bost organism. When such heterologous gene products are secreted rather than accumulated within the host, they are less likely to interfere with normal cellular functions. Second, some proteins that are inactive when produced intracellularly are active when secreted. Third, secretion into the medium avoids the necessity of breaking open the host cells in order to recover the product. Product purification is much easier and cost effective when product is present in the growth medium. And, fourth, since the recombinant product is present in the nutrient medium, the desired product can be continuously removed and the media can be recycled.

Most secreted proteins are expressed initially inside the cell in a precursor or a pre-protein form, containing an appended amino terminal extension called a signal peptide. The signal peptide plays an essential role in transporting the appended polypeptide into and/or through the limiting cellular membranes. This signal peptide is then cleaved proteolytically by a signal peptidase during or after secretion to yield a mature protein product.

Secretion of a heterologous or foreign protein can be accomplished by linking the coding sequence of the heterologous DNA to DNA encoding a signal peptide. It would be desirable to isolate a signal sequence encoding this signal peptide, which would facilitate secretion.

Signal sequences are especially useful in the creation of expression vectors. The use of such vectors would make it possible to transform compatible host cells so that they produce and secrete heterologous gene products. Examples of leader sequences which have been used to successfully secrete recombinant proteins from yeast bosts include those from the *Saccbaromyces cerevisiae* alpha mating factor a mating factor, and killer toxin genes. Isolation of a signal sequence from a methylotrophic yeast, such as *Pichia pastoris*, has not been described.

Conveniently, the promoter which is employed in such vectors to regulate expression of the heterologous gene products may be the promoter natively associated with the signal sequence. It would be especially advantageous if the promoter natively associated with the signal sequence provides for a high level of DNA transcription and is responsive to exogenous environmental stimuli. An example of such a promoter is the 5' regulatory region of the *Pichia pastoris* acid phosphatase (PHO1) gene (SEQ ID NO:3), which is transcribed at a high level in response to the absence of phosphate in the media, and repressed by the presence of phosphate in the media.

It is often desirable to transform a *Pichia pastoris* host with a recombinant DNA construct that will integrate at a precise position in the *Pichia pastoris* genome. The 5' and 3' sequences which flank the *Pichia pastoris* PHO1 gene, also known as first and second insertable DNA fragments, respectively, are used in expression vectors to direct the integration of the recombinant sequences at the PHO1 locus. The ability to integrate recombinant DNAs at the PHO1 locus is advantageous for at least two reasons: 1) in the development of *Pichia pastoris* expression strains having multiple copies of the same or different expression cassettes at the PHO1 locus or another Pichia locus, or 2) stable integration of one or more expression cassettes at the PHO1 locus only, in a host *Pichia pastoris* strain wherein disruption of an essential gene or a gene of the methanol metabolism pathway is undesirable.

Cells in which the PHO1 gene has been disrupted show a concomitant loss of acid phosphatase enzyme activity. The Pho⁻ phenotype, indicative of PHO1 gene disruption, may be screened for by plating the cells on low phosphate indicator plates and allowing colonies to grow overnight. Colonies in which the PHO1 gene is disrupted are white, whereas those colonies having an intact PHO1 gene are green. This colorimetric screen provides a rapid and easy method for detecting cells which have integrated expression cassettes correctly at the PHO1 locus and thus disrupted it.

Thus, it would be a significant contribution to the art to isolate a signal sequence that would facilitate the secretion of proteins from a host cell.

Additionally, it would be advantageous to isolate a 5' regulatory region which would provide for high levels of DNA transcription and is responsive to exogenous environmental stimuli. Currently no 5' regulatory region is known in the art which is transcribed at a high level in response to the absence of phosphate in the media and which can be used with the higbly productive fermentation yeast *Pichia pastoris*.

It would additionally be advantageous to isolate the acid phosphatase (AP) structural gene.

It would also be advantageous to provide novel vectors comprising fragments of the acid phosphatase gene.

It would additionally be advantageous to isolate a 3' transcription termination sequence.

It would also be advantageous to provide integrative vectors which would direct integration at the *Pichia pastoris* PHO1 locus.

It would additionally be advantageous to provide a method of identifying disruptants.

Thus, it is an object of the present invention to provide a signal sequence which facilitates the secretion of proteins from cells.

It is also an object of this invention to provide a 5' regulatory region transcribed in response to the absence of phosphate.

Another object of the present invention is to provide the DNA sequence of the *Pichia pastoris* acid phosphatase structural gene (SEQ ID NO:6).

It is a further object of this invention to provide novel vectors comprising a regulatory region and/or signal sequence operably-linked to a heterologous DNA sequence which encodes at least one polypeptide, and means of inducing said regulatory region to facilitate expression of said heterologous DNA sequence.

It is a still further object of this invention to provide a 3' transcription termination sequence from the acid phosphatase gene.

Yet another object of this invention is to provide integrative vectors which would direct integration at the *Pichia pastoris* PHO1 locus.

A further object of this invention is to provide a method of identifying disruptants.

Other aspects, objects, and advantages of the present invention will become apparent from the following specification, examples, and claims.

SUMMARY OF THE INVENTION

In accordance with the present invention, there is provided a novel DNA fragment comprising the signal sequence from the *Pichia pastoris* acid phosphatase gene (SEQ ID NO:4) which facilitates the secretion of proteins from cells.

A further aspect of this invention provides a novel DNA fragment comprising the *Pichia pastoris* acid phosphatase 5' regulatory region (SEQ ID NO:2).

In still another aspect of this invention there is provided a novel DNA fragment comprising the DNA sequence of the *Pichia pastoris* acid phosphatase (AP) structural gene (SEQ ID NO:6).

Yet another aspect of this invention provides novel vectors comprising the regulatory region and/or signal sequence operably-linked to a beterologous DNA sequence which encodes at least one polypeptide, and means of inducing said regulatory region to facilitate expression of said heterologous DNA sequence.

In another aspect of this invention there is provided novel DNA vectors comprising a 3' transcription termination sequence from the Pichia oris acid phosphatase gene (SEQ ID NO:8).

Another aspect of this invention provides integrative vectors which direct integration of the vector at the *Pichia pastoris* PHO1 locus.

Yet another aspect of this invention is to provide a method of identifying disruptants.

DETAILED DESCRIPTION OF THE INVENTION

Figure 1:
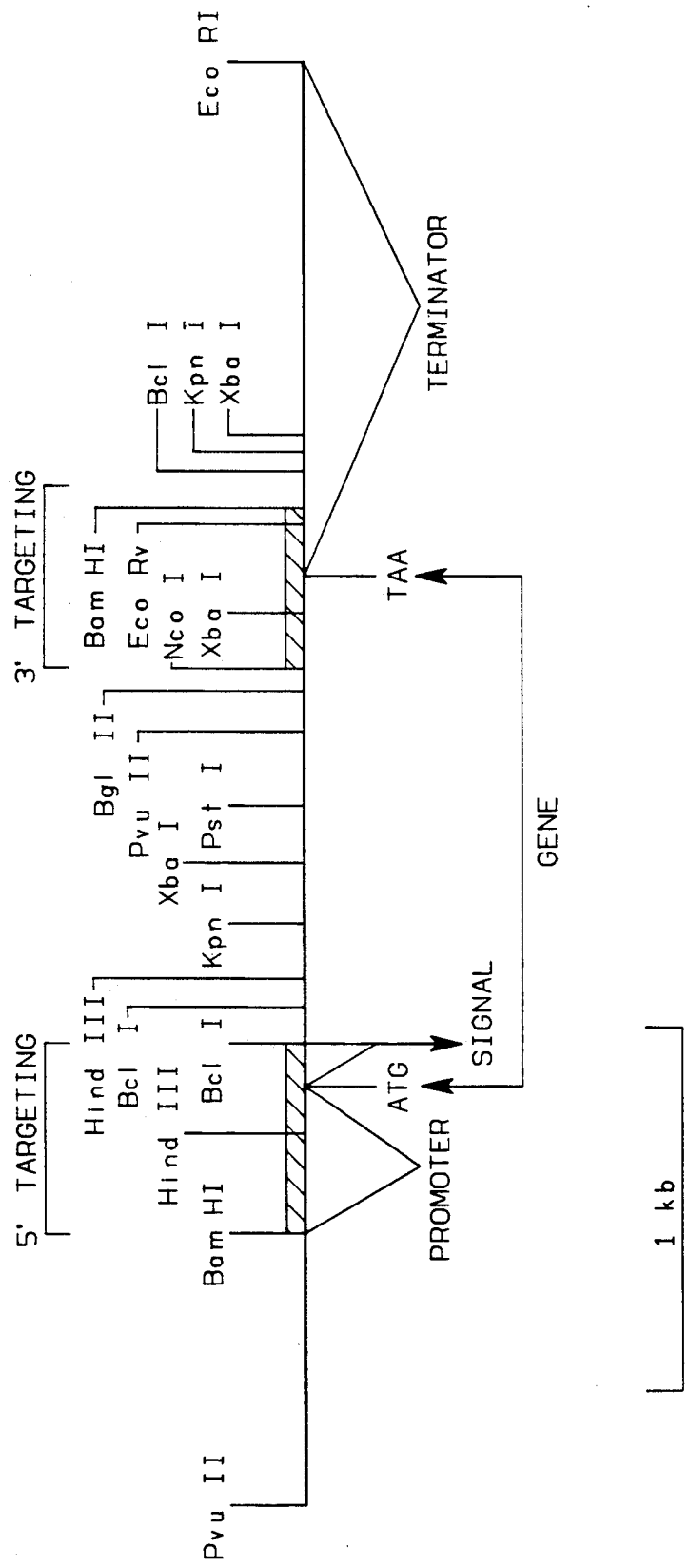
FIG. 1 provides a restriction map of the *Pichia pastoris* acid phosphatase gene (SEQ ID NO:1).

The present invention provides a novel isolated DNA fragment comprising an acid phosphatase gene, including its promoter (or 5' regulatory region), signal, transcription terminator, and flanking sequences, derived from *Pichia pastoris* (SEQ ID NO:1).

Acid phosphatase (AP) is an extracellular enzyme secreted by *Pichia pastoris* and other yeasts under conditions of inorganic phosphate starvation. The secreted acid phosphatase catalyzes the removal of phosphate from organic substrates, thus availing the phosphate for cell growth and survival.

The gene coding for acid phosphatase has been isolated and studied in several yeast species, and the regulatable nature of acid phosphatase gene expression bas been localized to the acid phosphatase promoter element. In conditions of low media concentrations of inorganic phosphate, the acid phosphatase promoter (or 5' regulatory region) is turned "on", the acid phosphatase gene is transcribed, and subsequently translated into the acid phosphatase enzyme. The newly synthesized acid phosphatase enzyme releases phosphate from organic substrates and makes the pbospbate available to the cell. The subsequent increase in phosphate concentration modulates the acid phosphatase promoter, resulting in decreased acid phosphatase gene transcription concomitant with the lessened need for acid phosphatase protein. Thus, the acid phosphatase promoter can be induced or repressed by low or high phosphate concentrations, respectively. Identification and isolation of the *Pichia pastoris* acid phosphatase promoter is significant. Because the regulation of acid phosphatase expression varies among the yeast species for which this expression has been analyzed, it is expected that the tight regulation observed for acid phosphatase expression in *Pichia pastoris* depends on the availability and use of the homologous promoter sequences.

Identification and isolation of the *Pichia pastoris* PHO1 gene signal sequence (SEQ ID NO:4) is significant in that, in addition to being the first signal sequence isolated from a *Pichia pastoris* gene, it represents the first signal sequence isolated from a metbylotrophic yeast. It has been discovered to be equivalent or superior to native gene signal sequences, e.g., the signal sequence from the tPA (Tissue Plasminogen Activator) or invertase genes, in directing secretion of beterologous proteins from *Pichia pastoris*, e.g., tPA or invertase.

It is often desirable to integrate recombinant expression vectors into the host genome instead of maintaining them as autonomously replicating elements. Integrated vectors are significantly more stable than autonomous vectors, and are preferred for the practice of the present invention. Specifically, linear site-specific integrative vectors as described in U.S. Pat. No. 4,882,279, which is herein incorporated by reference, are preferred. Such vectors comprise a serially arranged sequence of at least 1) a first insertable DNA fragment; 2) a selectable marker gene; and 3) a second insertable DNA fragment.

The first and second insertable DNA fragments are each at least about 200 nucleotides in length and have nucleotide sequences which are homologous to portions of the genomic DNA of the species to be transformed. The various components of the integrative vector are serially arranged forming a linear fragment of DNA such that the expression cassette and the selectable marker gene are positioned between the 3' end of the first insertable DNA fragment and the 5' end of the second insertable DNA fragment. The first and second insertable DNA fragments are oriented with respect to one another in the serially arranged linear fragment as they are so oriented in the parent genome.

Nucleotide sequences useful as the first and second insertable DNA fragments are nucleotide sequences which are homologous with separate portions of the native genomic site at which genomic modification is to occur. Thus, for example, if genomic modification is to occur at the locus of the acid phosphatase gene, the first and second insertable DNA fragments employed must be sequences homologous to seoarate portions of the acid phosphatase gene locus. For genomic modification to occur, the two insertable DNA fragments must be oriented with respect to one another in the linear fragment in the same relative orientation as they exist in the parent genome. Examples of nucleotide sequences which could be used as the first and second insertable DNA fragments are nucleotide sequences selected from the group consisting of the acid phosphatase PHO1 gene, alcohol oxidase AOX1 gene, histidinol dehydrogenase HIS4 gene, and the dihydroxyacetone synthetase DHAS gene.

The first insertable DNA fragment may contain an operable regulatory region which may comprise the regulatory region used in the expression cassette. The use of the first insertable DNA fragment as the regulatory region for an expression cassette is a preferred embodiment of the invention. Optionally, an insertion site or sites and a 3' termination sequence may be placed immediately 3' to the first insertable DNA fragment. This conformation of the linear site-specific integrative vector has the additional advantage of providing a ready site for insertion of a structural gene without nessessitating the addition of a compatible 3' termination sequence.

It is also necessary to include at least one selectable marker gene in the DNA used to transform the host strain. This facilitates selection and isolation of those organisms which have incorporated the transforming DNA. The marker gene confers a phenotypic trait to the transformed organism which the host did not have, e.g., restoration of the ability to produce a specific amino acid where the untransformed bost has a defect in the specific amino acid biosynthetic pathway or resistance to antibiotics and the like. Exemplary selectable marker genes may be selected from the group consisting of the HIS4 gene and the ARG4 gene from *Pichia pastoris* and *Saccharomvces cerevisiae*, the invertase gene (SUC2) from *Saccharomyces cerevisiae*, and the G418R kanamycin resistance gene from the *E.coli* transposable elements Tn601 or Tn903.

If the first insertable DNA fragment does not contain a regulatory region, a suitable regulatory region will need to be inserted operably linked to the structural gene, in order to provide an operable expression cassette. Similarly, if no 3' termination sequence is provided at the insertion site to complete the expression cassette, a 3' termination sequence will have to be operably linked to the structural gene to be inserted.

It is important that integration occur at a position in the genome that will not have a deleterious effect on the host cell. It was a surprising discovery that integration of a recombinant expression construct at the *Pichia pastoris* acid phosphatase gene locus (PHO1) was not deleterious to the Pichia host and led to stable integration of the recombinant sequences. Directed integration at the PHO1 locus is accomplished by the use of the 5' and 3' sequences which flank the *Pichia pastoris* PHO1 gene (which are also refererred to as first and second insertable DNA fragments), in recombinant expression vectors.

A further discovery was a method for screening transformed cells to identify those which integrated the expression vector sequences by disrupting the PHO1 locus. Cells in which the PHO1 gene has been disrupted show a concomitant loss of acid phosphatase enzyme activity. The Pho⁻ phenotype, indicative of PHO1 disruption, may be screened for by plating the cells on low phosphate indicator plates and allowing colonies to grow overnight. Colonites in which the PHO1 gene is disrupted are white, whereas those colonies having an intact PHO1 gene are green. This colorimetric screen provides a rapid and easy method for detecting cells which have integrated expression cassettes correctly at the PHO1 locus.

A partial restriction map of the *Pichia pastoris* acid phosphatase gene (SEQ ID NO:1) is depicted in FIG. 1. This gene has been further characterized by the nucleotide sequence which is provided in Table 1.

Also provided by the present invention are novel DNA fragments comprising the *Pichia pastoris* acid phosphatase 5' regulatory region (SEQ ID NO:3), signal sequence (SEQ ID NO:4), structural gene (SEQ ID NO:6), and 3' transcription termination sequence (SEQ ID NO:8).

The following Tables denote the sequences of the *Pichia pastoris* acid phosphatase gene (SEQ ID NO:1) and fragments thereof.

TABLE 1

Acid Phosphatase Gene
SEQ ID NOS:1 and 2

| BamHI | −390 | −370 | −350 |

GGATCCCTATTGTTACTTTTGCTTAACATTCCAATATTCTTCAACGGTTAATTGATTAAC

−330                    −310                    −290
ACTGTAACCTCTGCCCATGTGCTTCATCCAAATCTGGTAATCTGCTTTCTATTTCTGCCA

−270                    −250                    −230
AAATAGTTAATCTATGAGACATGTGCCCTCAATTGCGCAGTAGATCGAGTGGAAGTCTTC

TABLE 1-continued

Acid Phosphatase Gene
SEQ ID NOS:1 and 2

```
            -210                      -190                      -170
TTTGCGTAACACTCAAAGTATATCCCTGTTAGTCTTTATTCACCTGTTGCTGCATTGGTG

-150                      -130                      -110
TCAGTTACCATTATTGTTTCCACTTGGAAAAGCTTGTTTTTTTTTGATAGCACAGAAACG

-90                       -70                       -50
TGGGCTCCGATAAGCTAAACTTCAACGAGAATATAAAAGCTGAAAAGATTCTTGTCAAGA

-30                       -10                        10
ACTTGTACAACGACCAATAAGTCTTTCAAGGCATCAGACATGTTTTCTCCTATTCTAAGT
                                                 Met Phe Ser Pro Ile Leu Ser 30                        50                        70
CTGGAAATTATTCTCGCTTTGGCTACTCTCCAATCAGTCTTTGCGGTTGAGTTGCAGCAC
Leu Glu Ile Ile Leu Ala Leu Ala Thr Leu Gln Ser Val Phe Ala Val Glu Leu Gln His 90                       110         BclI         130
GTTCTTGGAGTCAACGACAGACCCTATCCTCAGAGGACAGATGATCAGTACAACATTCTG
Val Leu Gly Val Asn Asp Arg Pro Tyr Pro Gln Arg Thr Asp Asp Gln Tyr Asn Ile Leu 150                       170                       190
AGACATCTGGGAGGCTTGGGCCCCTACATCGGTTACAATGGATGGGGAATTGCTGCTGAG
Arg His Leu Gly Gly Leu Gly PRo Tyr Ile Gly Tyr Asn Gly Trp Gly Ile Ala Ala Glu 210                       230                       250
TCTGAAATTGAATCCTGTACGATTGATCAGGCTCATCTGTTGATGAGACATGGAGAAAGA
Ser Glu Ile Glu Ser Cys Thr Ile Asp Gln Ala His Leu Leu Met Arg His Gly Glu Arg 270                       290                       310
TACCCAAGTACCAATGTGGGGAAACAACTAGAAGCTTTGTACCAGAAACTACTAGATGCT
Tyr Pro Ser Thr Asn Val Gly Lys Gln Leu Glu Ala Leu Tyr Gln Lys Leu Leu Asp Ala 330                       350                       370
GATGTGGAAGTCCCTACAGGACCATTGTCTTTCTTTCAAGACTATGATTACTTCGTCTCT
Asp Val Glu Val Pro Thr Gly Pro Leu Ser Phe Phe Gln Asp Tyr Asp Tyr Phe Val Ser 390                       410                       430
GACGCCGCTTGGTACGAGCAAGAAACAACTAAGGGTTTCTACTCGGGGTTAAACACCGCT
Asp Ala Ala Trp Tyr Glu Gln Glu Thr Thr Lys Gly Phe Tyr Ser Gly Leu Asn Thr Ala 450                       470                       490
TTCGATTTTGGTACCACTTTGAGAGAACGATATGAACATTTGATAAACAATAGCGAAGAA
Phe Asp Phe Gly Thr Thr Leu Arg Glu Arg Tyr Glu His Leu Ile Asn Asn Ser Glu Glu 510                       530                       550
GGAAAGAAACTTTCTGTTTGGGCTGGCTCTCAAGAAAGAGTTGTTGACAACGCAAAGTAC
Gly Lys Lys Leu Ser Val Trp Ala Gly Ser Gln Glu Arg Val Val Asp Asn Ala Lys Tyr 570                       590                       610
TTTGCTCAAGGATTTATGAAATCTAACTACACCGTTATGGTCGAAGTCGTTGCTCTAGAA
Phe Ala Gln Gly Phe Met Lys Ser Asn Tyr Thr Val Met Val Glu Val Val Ala Leu Glu 630                       650                       670
GAGGAGAAATCCCAGGGACTCAACTCTCTAACGGCTCGAATTTCATGTCCAAACTATAAC
Glu Glu Lys Ser Gln Gly Leu Asn Ser Leu Thr Ala Arg Ile Ser Cys Pro Asn Tyr Asn 690                       710                       730
AGCCATATCTACAAAGATGGCGACTTGGGGAATGACATTGCTCAAAGAGAAGCTGACAGA
Ser His Ile Tyr Lys Asp Gly Asp Leu Gly Asn Asp Ile Ala Gln Arg Glu Ala Asp Arg 750                       770                       790
TTGAACACTCTTTCTCCAGGATTTAACATTACTGCAGATGATATTCCAACAATTGCCCTA
Leu Asn Thr Leu Ser Pro Gly Phe Asn Ile Thr Ala Asp Asp Ile Pro Thr Ile Ala Leu 810                       830                       850
TACTGTGGCTTTGAACTAAATGTAAGAGGTGAGTCATCCTTCTGTGACGTCTTGTCAAGA
Tyr Cys Gly Phe Glu Leu Asn Val Arg Gly Glu Ser Ser Phe Cys Asp Val Leu Ser Arg 870                       890                       910
GAGGCTCTACTGTACACTGCTTATCTTAGAGATTTGGGATGGTATTACAATGTTGGAAAC
Glu Ala Leu Leu Tyr Thr Ala Tyr Leu Arg Asp Leu Gly Trp Tyr Tyr Asn Val Gly Asn 930                       950                       970
GGGAACCCACTTGGAAAGACAATCGGCTACGTCTATGCCAACGCCACAAGACAGCTGTTG
Gly Asn Pro Leu Gly Lys Thr Ile Gly Tyr Val Tyr Ala Asn Ala Thr Arg Gln Leu Leu
```

TABLE 1-continued

Acid Phosphatase Gene
SEQ ID NOS:1 and 2

```
         990                1010                1030
GAAAACACAGAAGCTGATCCTAGAGATTATCCTTTGTACTTTTCCTTTAGTCATGATACC
Glu Asn Thr Glu Ala Asp Pro Arg Asp Tyr Pro Leu Tyr Phe Ser Phe Ser His Asp Thr 1050               1070                1090
GATCTGCTTCAAGTATTCACTTCACTCGGTCTTTTCAACGTGACAGATCTGCCATTAGAC
Asp Leu Leu Gln Val Phe Thr Ser Leu Gly Leu Phe ASn Val Thr Asp Leu Pro Leu Asp 1110               1130                Ncol
CAGATTCAATTCCAGACCTCTTTCAAATCTACCGAAATAGTTCCCATGGGAGCAAGATTG
Gln Ile Gln Phe Gln Thr Ser Phe Lys Ser Thr Glu Ile  Val Pro Met Gly Ala Arg Leu 1170               1190                1210
CTTACCGAGAGATTATTGTGTACTGTTGAAGGTGAAGAAAAATACTACGTTAGAACTATC
Leu Thr Glu Arg Leu Leu Cys Thr Val Glu Gly Glu Glu Lys Tyr Tyr Val Arg Thr Ile 1230               1250                1270
CTCAACGATGCAGTCTTCCCACTGAGTGACTGTTCCTCTGGCCCTGGATTCTCTTGTCCG
Leu Asn Asp Ala Val Phe Pro Leu Ser Asp Cys Ser Ser Gly Pro Gly Phe Ser Cys Pro 1290               1310                1330
TTGAACGATTATGTTTCTAGACTTGAGGCATTGAACGAGGACAGTGACTTTGCGGAAAAC
Leu Asn Asp Tyr Val Ser Arg Leu Glu Ala Leu Asn Glu Asp Ser Asp Phe Ala Glu Asn 1350               1370                1390
TGTGGAGTTCCTAAAAATGCTTCCTACCCACTTGAACTATCATTCTTCTGGGATGACTTG
Cys Gly Val Pro Lys Asn Ala Ser Tyr Pro Leu Glu Leu Ser Phe Phe Trp Asp Asp Leu 1410               1430                1450
TCATAAAAATGGTAAGGAATGTTTTGCATCAGATACGAGTTCAAAACGATTAAGAAGAGA
Ser End 1470               1490                1510
ATGCTCTTTTTTTTGTTTCTATCCAATTGGACTATTTTCGTTTATTTTAAATAGCGTACA 1530               1550                1570
ACTTTAACTAGATGATATCTTCTTCTTCAAACGATACCACTTCTCTCATACTAGGTGGAG BamHI
GTTCAATGGATCC
```

TABLE 2

5' Regulatory Region
SEQ ID NO:3:

```
BamHI  -390              -370                -350
GGATCCCTATTGTTACTTTTGCTTAACATTCCAATATTCTTCAACGGTTAATTGATTAAC

-330              -310                -290
ACTGTAACCTCTGCCCATGTGCTTCATCCAAATCTGGTAATCTGCTTTCTATTTCTGCCA

-270              -250                -230
AAATAGTTAATCTATGAGACATGTGCCCTCAATTGCGCAGTAGATCGAGTGGAAGTCTTC

-210              -190                -170
TTTGCGTAACACTCAAAGTATATCCCTGTTAGTCTTTATTCACCTGTTGCTGCATTGGTG

-150              -130                -110
TCAGTTACCATTATTGTTTCCACTTGGAAAAGCTTGTTTTTTTTTGATAGCACAGAAACG

-90               -70                 -50
TGGGCTCCGATAAGCTAAACTTCAACGAGAATATAAAAGCTGAAAAGATTCTTGTCAAGA

-30               -10
ACTTGTACAACGACCAATAAGTCTTTCAAGGCATCAGAC
```

TABLE 3

Signal Sequence
SEQ ID NOS:4 and 5

```
                                    10
                           ATGTTTTCTCCTATTCTAAGT
        PHO1 signal sequence ──▶ Met Phe Ser Pro Ile  Leu Ser
```

TABLE 3-continued

Signal Sequence
SEQ ID NOS:4 and 5

```
         30                        50
CTGGAAATTATTCTCGCTTTGGCTACTCTCCAATCAGTCTTTGCG
Leu Glu Ile Ile Leu Ala Leu Ala Thr Leu Gln Ser Val Phe Ala
```

TABLE 4

Acid Phosphatase
Structural Gene
SEQ ID NOS:6 and 7

```
                                                                70
                                                        GTTGAGTTGCAGCAC
                                                        Val Glu Leu Gln His 90                      110              BclI    130
GTTCTTGGAGTCAACGACAGACCCTATCCTCAGAGGACAGATGATCAGTACAACATTCTG
Val Leu Gly Val Asn Asp Arg Pro Tyr Pro Gln Arg Thr Asp Asp Gln Tyr Asn Ile Leu 150                      170                      190
AGACATCTGGGAGGCTTGGGCCCCTACATCGGTTACAATGGATGGGGAATTGCTGCTGAG
Arg His Leu Gly Gly Leu Gly PRo Tyr Ile  Gly Tyr Asn Gly Trp Gly Ile Ala Ala Glu 210                      230                      250
TCTGAAATTGAATCCTGTACGATTGATCAGGCTCATCTGTTGATGAGACATGGAGAAAGA
Ser Glu Ile  Glu Ser Cys Thr Ile  Asp Gln Ala His Leu Leu Met Arg His Gly Glu Arg 270                      290                      310
TACCCAAGTACCAATGTGGGGAAACAACTAGAAGCTTTGTACCAGAAACTACTAGATGCT
Tyr Pro Ser Thr Asn Val Gly Lys Gln Leu Glu Ala Leu Tyr Gln Lys Leu Leu Asp Ala 330                      350                      370
GATGTGGAAGTCCCTACAGGACCATTGTCTTTCTTTCAAGACTATGATTACTTCGTCTCT
Asp Val Glu Val Pro Thr Gly Pro Leu Ser Phe Phe Gln Asp Tyr Asp Tyr Phe Val Ser 390                      410                      430
GACGCCGCTTGGTACGAGCAAGAAACAACTAAGGGTTTCTACTCGGGGTTAAACACCGCT
Asp Ala Ala Trp Tyr Glu Gln Glu Thr Thr Lys Gly Phe Tyr Ser Gly Leu Asn Thr Ala 450                      470                      490
TTCGATTTTGGTACCACTTTGAGAGAACGATATGAACATTTGATAAACAATAGCGAAGAA
Phe Asp Phe Gly Thr Thr Leu Arg Glu Arg Tyr Glu His Leu Ile  Asn Asn Ser Glu Glu 510                      530                      550
GGAAAGAAACTTTCTGTTTGGGCTGGCTCTCAAGAAAGAGTTGTTGACAACGCAAAGTAC
Gly Lys Lys Leu Ser Val Trp Ala Gly Ser Gln Glu Arg Val Val Asp Asn Ala Lys Tyr 570                      590                      610
TTTGCTCAAGGATTTATGAAATCTAACTACACCGTTATGGTCGAAGTCGTTGCTCTAGAA
Phe Ala Gln Gly Phe Met Lys Ser Asn Tyr Thr Val Met Val Glu Val Val Ala Leu Glu 630                      650                      670
GAGGAGAAATCCCAGGGACTCAACTCTCTAACGGCTCGAATTTCATGTCCAAACTATAAC
Glu Glu Lys Ser Gln Gly Leu Asn Ser Leu Thr Ala Arg Ile  Ser Cys Pro Asn Tyr Asn 690                      710                      730
AGCCATATCTACAAAGATGGCGACTTGGGGAATGACATTGCTCAAAGAGAAGCTGACAGA
Ser His Ile  Tyr Lys Asp Gly Asp Leu Gly Asn Asp Ile  Ala Gin Arg Glu Ala Asp Arg 750                      770                      790
TTGAACACTCTTTCTCCAGGATTTAACATTACTGCAGATGATATTCCAACAATTGCCCTA
Leu Asn Thr Leu Ser Pro Gly Phe Asn Ile  Thr Ala Asp Asp Ile  Pro Thr Ile  Ala Leu 810                      830                      850
TACTGTGGCTTTGAACTAAATGTAAGAGGTGAGTCATCCTTCTGTGACGTCTTGTCAAGA
Tyr Cys Gly Phe Glu Leu Asn Val Arg Gly Glu Ser Ser Phe Cys Asp Val Leu Ser Arg 870                      890                      910
GAGGCTCTACTGTACACTGCTTATCTTAGAGATTTGGGATGGTATTACAATGTTGGAAAC
Glu Ala Leu Leu Tyr Thr Ala Tyr Leu Arg Asp Leu Gly Trp Tyr Tyr Asn Val Gly Asn 930                      950                      970
GGGAACCCACTTGGAAAGACAATCGGCTACGTCTATGCCAACGCCACAAGACAGCTGTTG
Gly Asn Pro Leu Gly Lys Thr Ile  Gly Tyr Val Tyr Ala Asn Ala Thr Arg Gin Leu Leu 990                     1010                     1030
GAAAACACAGAAGCTGATCCTAGAGATTATCCTTTGTACTTTTCCTTTAGTCATGATACC
Glu Asn Thr Glu Ala Asp Pro Arg Asp Tyr Pro Leu Tyr Phe Ser Phe Ser His Asp Thr
```

TABLE 4-continued

Acid Phosphatase Structural Gene
SEQ ID NOS:6 and 7

```
     1050                    1070                     1090
GATCTGCTTCAAGTATTCACTTCACTCGGTCTTTTCAACGTGACAGATCTGCCATTAGAC
Asp Leu Leu Gln Val Phe Thr Ser Leu Gly Leu Phe ASn Val Thr Asp Leu Pro Leu Asp 1110                    1130                     Ncol
CAGATTCAATTCCAGACCTCTTTCAAATCTACCGAAATAGTTCCCATGGGAGCAAGATTG
Gln Ile Gln Phe Gln Thr Ser Phe Lys Ser Thr Glu Ile Val Pro Met Gly Ala Arg Leu 1170                    1190                     1210
CTTACCGAGAGATTATTGTGTACTGTTGAAGGTGAAGAAAAATACTACGTTAGAACTATC
Leu Thr Glu Arg Leu Leu Cys Thr Val Glu Gly Glu Glu Lys Tyr Tyr Val Arg Thr Ile 1230                    1250                     1270
CTCAACGATGCAGTCTTCCCACTGAGTGACTGTTCCTCTGGCCCTGGATTCTCTTGTCCG
Leu Asn Asp Ala Val Phe Pro Leu Ser Asp Cys Ser Ser Gly Pro Gly Phe Ser Cys Pro 1290                    1310                     1330
TTGAACGATTATGTTTCTAGACTTGAGGCATTGAACGAGGACAGTGACTTTGCGGAAAAC
Leu Asn Asp Tyr Val Ser Arg Leu Glu Ala Leu Asn Glu Asp Ser Asp Phe Ala Glu Asn 1350                    1370                     1390
TGTGGAGTTCCTAAAAATGCTTCCTACCCACTTGAACTATCATTCTTCTGGGATGACTTG
Cys Gly Val Pro Lys Asn Ala Ser Tyr Pro Leu Glu Leu Ser Phe Phe Trp Asp Asp Leu TCATAA
Ser End
```

TABLE 5

3' Transcription Termination Sequence
SEQ ID NO:8:

```
     1410                    1430                     1450
       AAATGGTAAGGAATGTTTTGCATCAGATACGAGTTCAAAACGATTAAGAAGAGA 1470                    1490                     1510
ATGCTCTTTTTTTTGTTTCTATCCAATTGGACTATTTTCGTTTATTTTAAATAGCGTACA 1530                    1550                     1570
ACTTTAACTAGATGATATCTTCTTCTTCAAACGATACCACTTCTCTCATACTAGGTGGAG

BamHI
GTTCAATGGATCC
```

The acid phosphatase gene is recovered from *Pichia pastoris* cultures such as *Pichia pastoris* NRRL Y-11430 by methods as set forth in the following Examples. A general method for recovering the *Pichia pastoris* acid phosphatase gene (SEQ ID NO:1) consists of using an acid phosphatase probe, such as the low phosphate (LP) probes described in the following examples, to screen a library of *Pichia pastoris* DNA. Other probes could be selected or synthesized based on the sequence disclosed in Table 1. Hybridization of the probes can be performed by any suitable protocol known to those skilled in the art. *Pichia pastoris* libraries can be prepared by techniques known in the art including but not limited to the method described by Cregg et al (1985), *Mol. Cell Bio.* 5, 3376-3385.

Alternatively, the acid phosphatase 5' regulatory region (SEQ ID NO:3), signal sequence (SEQ ID NO:4), structural gene (SEQ ID NO:6), and 3' regulatory region (SEQ ID NO:8) may be obtained by synthesizing the appropriate sequence as defined in Tables 1-5 using known enzymatic or chemical means. Suitable means include but are not limited to chemical procedures based on pbosphotriester, pbophite, or cyanoethylphosphoramidite chemistry.

Those skilled in the art will also recognize that the isolated *Pichia pastoris* acid phosphatase 5' regulatory region (SEQ ID No:3), signal sequence (SEQ ID NO:4), structural gene (SEQ ID NO:6), and 3' transcriptional termination sequence (SEQ ID NO:8) of the present invention as compared to subsequently isolated *Pichia pastoris* acid phosphatase 5' regulatory region, signal sequence, structural gene, and 3' transcriptional termination sequences may contain a de minimis number of nucleotide differences due to clonal variation or sequencing error which may occur.

Modification of the *Pichia pastoris* acid phosphatase 5' regulatory region (SEQ ID NO:3), signal sequence (SEQ ID NO:4), structural gene (SEQ ID NO:6), and 3' transcriptional termination sequence (SEQ ID NO:8) can also be performed, such as adding linker DNA, or performing mutagenesis (for example M13 mutagenesis) to provide or remove restriction site(s) and the like.

Once the *Pichia pastoris* acid phosphatase gene is recovered, it may be maintained or replicated in eucaryotic or procaryotic plasmed-host systems, such as pBR322 maintained in *E. coli*, or in any other suitable system known in the art.

Those skilled in the art will also recognize that numerous additional DNA sequences can also be incorporated into the vector employed, such as bacterial plasmid DNA, various marker genes, bacteriophage DNA, autonomous replicating sequences, and centromeric DNA, to name only a few representative examples.

The acid phosphatase 5' regulatory region (SEQ ID NO:3) is contained within the DNA fragment extending from nucleotide −399 to about nucleotide 0, as shown in FIG. 1 and Table 2. This fragment is capable of effecting the transcription of DNA to RNA when operably linked to and positioned at the 5' end of a heterologous DNA sequence coding for at least one polypeptide.

To utilize the acid phosphatase 5' regulatory region (SEQ ID NO:3) disclosed herein, the fragment described in FIG. 1 and Table 2 can be operably linked to heterologous DNA sequences encoding at least one polypeptide. For the purpose of this specification heterologous DNA sequences are combinations of DNA sequences which do not naturally occur in the host or in association with said regulatory region. Suitable heterologous DNA sequences encoding at least one polypeptide which could be operably linked with the acid phosphatase 5' regulatory region (SEQ ID NO:3) include but are not limited to tissue plasminogen activator, human serum albumin, and invertase. Heterologous DNA sequences used with the present invention should contain a 5' ATG start codon, a 3' stop codon and may additionally include nucleotide sequences which function to stabilize the MRNA, or to direct polyadenylation.

The combination of the acid phosphatase 5' regulatory region (SEQ ID NO:3) operably linked to a heterologous DNA sequence may be inserted in a suitable vector. Numerous yeast vector-host combinations are possible and are known to those skilled in the art. Additional sequences such as marker genes or other sequences which render the vector capable of growth amplification and rapid propagation in bacteria or yeast may also be present.

Suitable host cells which can be transformed with a vector containing the acid phosphatase 5' regulatory region include yeast such as those from the genera of Saccharomyces, Pichia and Hansenula, preferably Pichia, and most preferably Pichia pastoris.

Transformation of a suitable host cell with a vector 3 containing the acid phosphatase 5' regulatory region (SEQ ID NO:3) can be accomplished by any suitable transformation technique known to those skilled in the art.

The acid phosphatase 5' regulatory region (SEQ ID NO:3) is controlled by the concentration of phosphate in the media. Specifically, this regulatory region is derepressed by low concentrations of phosphate. Therefore, the 5' regulatory region is regulated by changing the concentration of phosphate present in the media.

The acid phosphatase signal sequence (SEQ ID NO:4) is contained within the DNA fragment extending from nucleotide 1 to about nucleotide 66 as shown in FIG. 1 and Table 3. To utilize the acid phosphatase signal sequence (SEQ ID NO:4) disclosed herein, the fragment described in FIG. 1 and Table 3 can be operably linked to heterologous DNA sequences encoding at least one polypeptide. Suitable heterologous DNA sequences include but are not limited to those DNA sequences selected from the group consisting of tissue plasminogen activator, human serum albumin, and invertase.

The combination of the acid phosphatase signal sequence (SEQ ID NO:4) operably linked to a heterologous DNA sequence may then be linked to a suitable promoter. Conveniently, the promoter which is employed may be the promoter associated with the leader sequence. Alternatively, one may replace the naturally occuring PHO1 promoter with other heterologous promoters which would allow for transcriptional regulation. An example of a suitable heterologous promoter would be the Pichia pastoris alcohol oxidase (AOX1) promoter (or 5' regulatory region) disclosed in U.S. Pat. No. 4,808,537, which is herein incorporated by reference.

Suitable vectors into which this DNA fragment containing the acid phosphatase signal sequence (SEQ ID NO:4) could be inserted may be obtained as described above. Additionally, suitable host cells which may be transformed with the resulting vector containing a DNA fragment coding for a signal sequence include yeast such as those from the genera Saccharomyces, Hansenula, and Pichia, with Pichia pastoris being preferred. Transformation of these host cells can be accomplished by any suitable means known to those skilled in the art. The signal sequence that is operably linked to a protein that has been produced by one of these vector/host systems may direct the secretion of said protein from the host cell.

The acid phosphatase structural gene (SEQ ID NO:6) is contained within the DNA fragment extending from nucleotide 67 to nucleotide 1407 as shown in 6FIG. 1 and Table 4. The acid phosphatase structural gene (SEQ ID NO:6) may be utilized in recombinant biotechnology for a variety of purposes including but not limited to: (a) DNA constructs for performing disruptive homologous recombination (a process for inserting heterologous DNA sequences into the Pichia pastoris genome at the acid phosphatase locus and thus disrupting the acid phosphatase gene activity, and (b) the production of acid phosphatase protein for use in various bioassays.

The acid phosphatase 3' transcription termination sequence (SEQ ID NO:8) terminates the transcription of mRNA or stabilizes mRNA when operably linked to the 3' end of a DNA sequence which codes for the production of a polypeptide. This acid phosphatase 3' transcription termination sequence (SEQ ID NO:8) is contained within the DNA fragment extending from nucleotide 1408 to about nucleotide 1594 as shown in FIG. 1 and Table 5. The acid phosphatase 3' transcription termination sequence (SEQ ID NO:8) may be operably linked to a heterologous DNA sequence which codes for a polypeptide, and used to terminate transcription of, or to stabilize mRNA in yeast such as those from the genera Saccharomvces. Hansenula, and Pichia, but it is particulary well suited for use in Pichia pastoris.

The following non-limiting Examples are provided to further illustrate the practice of the present invention.

EXAMPLES

Strains

The following strains have been used in these Examples:

Pichia pastoris KM71 (AOX1, his4)
Pichia pastoris GS115 (his4) NRRL Y-15851
Pichia pastoris GS190 (arg4) NRRL Y-18014
Pichia pastoris GS247 (Ade-)
Pichia pastoris KM71:GS102 (Mut−)
Pichia pastoris GS115:GS102 (Mut +)
Pichia pastoris MD100-20 (his4, Ade−)
Pichia pastoris MB102-26 (pho−, his4, ade−)
Pichia pastoris MB102-28

Pichia pastoris MB102-51
Pichia pastoris KM71:pPSU216 (Mut⁻)
Pichia pastoris GS115:pPSU216 (Mut⁺)
E. coli. JM103 delta (lac pro) thi rpsl (strA) supE end A sbcB hsdR
Bowes melanoma tPA over-expressing cell line ATCC# CRL9607 (human melanoma cells)

Media, Buffers, and Solutions

The media, buffers, and solutions employed in the following Examples bave the compositions indicated below:

| LP Media (low phosphate) | |
|---|---|
| biotin | 2 µg/L |
| calcium pantothenate | 400 µg/L |
| folic acid | 2 µg/L |
| nicotinic acid | 400 µg/L |
| p-aminobenzoic acid | 2 µg/L |
| pyridoxine hydrochloride | 400 µg/L |
| riboflavin | 200 µg/L |
| thiamine-HCl | 400 µg/L |
| boric acid | 500 µg/L |
| cupric sulfate | 40 µg/L |
| potassium iodide | 100 µg/L |
| ferric chloride | 200 µg/L |
| manganese sulfate | 400 µg/L |
| zinc sulfate | 400 µg/L |
| inositol | 2 mg/L |
| sodium molybdate | 200 µg/L |
| ammonium sulfate | 5 g/L |
| monobasic potassium phosphate | 30 mg/L |
| potassium chloride | 1.5 g/L |
| sodium chloride | 1.7 mM |
| calcium chloride | 0.68 mM |
| magnesium sulfate | 4.2 mM |
| TE Buffer | |
| Tris-HCl, pH 8.0 | 10 mM |
| EDTA | 1 mM |
| SSPE (1X) | |
| NaCl | 180 mM |
| Na₃PO₄, pH 7.7 | 10 mM |
| EDTA | 1 mM |
| SSC (1X) | |
| NaCl | 150 mM |
| Na citrate | 15 mM |
| Denhardt's solution (1X) | |
| Ficoll | 200 mg/L |
| polyvinylpyrrolidone | 200 mg/L |
| bovine serum albumin | 200 mg/L |
| REB | |
| LiCl | 100 mM |
| Tris-HCl, pH 7.4 | 100 mM |
| EDTA | 0.1 mM |
| PCI | |
| phenol | 500 ml/L |
| chloroform | 480 ml/L |
| isoamyl alcohol | 20 ml/L |
| CI | |
| chloroform | 960 ml/L |
| isoamyl alcohol | 40 ml/L |
| LP Indicator plates, 1 liter | IX LP media |
| | 22.5 mM citric acid pH 4.8 |
| | 20 g dextrose |
| | 60 mg 5-bromo,4-chloro, 3-indolyl phosphate (Sigma) |
| | 25 g Noble agar (Difco) |
| SCE Buffer | 9.1 g sorbitol |
| | 1.47 g sodium citrate |
| | 0.168 g EDTA |
| | pH to 5.8 with HCl in 50 ml |
| | dH20 and autoclave |
| YNB Media | 6.75 g yeast nitrogen base without amino acids (DIFCO) in 1 L of water |

EXAMPLE I

Construction of pLP24

In order to isolate and characterize the acid phosphatase gene from Pichia pastoris (SEQ ID NO:1), the following experiments were performed. Pichia pastoris GS115 (NRRL Y-15851) was grown in both a high phosphate (HP) environment [comprised of yeast nitrogen base minus amino acids (DIFCO), 2% dextrose, and 20 mg/l histidine] and in a low phosphate (LP) environment [comprised of LP media, 2% dextrose, and 20 mg/l histidine], each in a 300 ml total volume. The cells were pelleted, washed once with 10 ml REB, and resuspended in 4 ml REB in a 30 ml Corex tube. 8 g of glass beads and 4 ml PCI were then added. The suspension was mixed on a vortex mixer at high speed, eight times at 20 seconds each, with cooling on ice for 20 seconds between mixings. The suspension was then centrifuged at 10,000×g for 10 min. The aqueous (top) layer was extracted twice with 4 ml PCI and 4 ml CI. The RNA was precipitated from the aqueous phase, at −20° C., with 0.1 volume of 3H potassium acetate, pH 5.2 and 2.5 volumes of ethanol. Poly A⁺ RNA was selected as per Maniatis et al. (Molecular Cloning, A Laboratory Manual), with LiCl substituted for NaCl. Synthesis of LP or HP mRNA-labeled CDNA probes, using 2 pg of each type of poly A + RNA, was also according to Maniatis et al.

60 ng of a purified Pichia pastoris plasmid library in YEP13 [Broach et al., Gene: 8121 (1979)] was used to transform E. coli. MC1061 (Mandel and Higa, 1970, J. Mol. Biol. 53:154). Approximately 8,000 colonies resulted. The colonies were replicated on duplicate nitrocellulose filters, amplified on LB plates containing 100 ug/ml ampicillin and 170 µg/ml chlorampbenicol, lysed by standard protocols (Grunstein and Wallis, 1979, Methods in Enzymology 68, 379–389), baked at 80° C. for 90 min., and separate filters were hybridized with either the LP or HP CDNA probes. Hybridization was performed using 2×SSPE, 1×Denhardt's solution, 0.2% sodium dodecyl sulfate (SDS), and 2.5×10⁵ cpm labeled cDNA probes per ml of hybridization solution. Hybridization was at 55° C. for 40 hours in a 25 ml total volume. Following hybridization, the filters were washed twice in 2×SSC, 0.1% SDS at room temperature and twice in 0.2×SSC, 0.1% SDS at 65° C., then dried and exposed to x-ray film.

Twenty-four genomic clones were identified that hybridized more strongly with the LP cDNA probe than with the HP cDNA probe and were therefore possible candidates to contain inserts that encoded the acid phosphatase gene. These 24 clones were rescreened as before with LP and HP probes, with 14 of the rescreened clones again bybridizing more strongly to the LP cDNA probe. Plasmid DNA was isolated from each of these 14 clones, digested with EcoRI, separated by agarose gel electrophoresis, blotted to duplicate nitrocellulose filters, and each filter was hybridized with either the LP or HP cDNA under the same conditions as before. Gene fragments from four separate clones hybridized strongly to the LP cDNA probe and weakly, or not at all, to the HP cDNA probe. These fragments were then restriction mapped using EcoRI+HindIII, EcoRI+SalI, and EcoRI+BamHI double digests and again hybridized with the LP cDNA probe. The fragments encoded unrelated phosphate-regulated gene segments as determined by the differences in their restriction maps.

The regions identified by this procedure as encoding LP-regulated genes were subcloned into pUC8 or pUC19 (New England Biolabs). The resultant plasmids were labeled with $^{32}P$ by nick translation (Maniatis). The labeled plasmids were used to probe RNA blots of LP and HP RNA (5μg/blot). One of the original 24 clones, identified as pLP24, was chosen for further study.

EXAMLE II

Construction of pLP2411

The plasmid pLP24 generated in Example I and thought to contain the *Pichia pastoris* acid phosphatase gene (SEQ ID NO:1) or a fragment thereof was further characterized in the following manner. 10 μg of pLP24 was digested with EcoRI/SalI and the 2.1 kb fragment was gel purified.

10 μg of pYM25 (NRRL B-18015) was digested with SphI/SalI and the 3.1 kb fragment was gel purified. 5 μg of pUC19 was digested with EcoRI/SalI, PCI extracted, CI extracted and ETOH precipitated. 100 ng of the EcoRI/SalI linearized pUC19 was ligated with 200 ng of the 2.1 kb EcoRI/SalI fragmerit of pLP24 and 450 ng of the 3.1 kb SphI/SalI fragment of pYM25, in a 3 part ligation, in 20 μl of ligation buffer+1 mm ATP+1U T4 DNA ligase. *E. coli* strain MC1061 was transformed and the correct plasmid was identified by the presence of a 2.1 kb EcoRI/SalI fragment and a 3.1 kb SphI/SalI fragment. The correct plasmid was called pLP2411.

EXAMPLE III

Construction of pLP2412 PHO1-Disruption Vector and Development of GS190:pLP2412

Plasmid pLP2411, derived from plasmid pLP24 (see Example II), was digested with XbaI, treated with Klenow DNA polymerase to generate blunt ends, and ligated with the 2.1 kb HpaI fragment from plasmid pYM25. This fragment contained the *Saccharomyces cerevisiae* ARG4 gene. (Plasmid pYM25 is available as NRRL B-18015). The resulting plasmid was designated pLP2412. pLP2412 was then digested with EcoRI and BamHI. The 3.3 kb fragment was isolated and used to transform *Pichia pastoris* GS190 (NRRL Y-18014) to Arg+ prototropy (the transformation procedure is described in Example IV). Arginine prototrophs were identified by their ability to grow in media lacking arginine. They were isolated and screened on LP indicator plates for the presence of acid phosphatase. The colonies were replica-plated to LP indicator plates and allowed to grow overnight at 30° C. Colonies on the LP indicator plates were either green (PHO1) or white (phol). White colonies were transformants containing the 3.3 kb expression cassette from above, stably integrated by disruption at the PHO1 locus of the *Pichia pastoris* genome.

Genomic DNAs from stable Arg+ strains were analyzed by Southern filter hybridization to determine the location of the expression cassette. The 3.3 kb EcoRI-BamHI fragment, containing the *Saccharomyces cerevisiae* ARG4 gene, had specifically integrated and disrupted the genomic sequence which was analogous to the DNA fragment contained in pLP2411, confirming that this locus coded for acid phosphatase (PHO1). This transformant was designated GS190:pLP2412.

EXAMPLE IV

Transformation of Pichica pastoris

The following protocol was used in the transformation of *Pichia pastoris*.

Yeast cells were inoculated into about 10 ml of YPD medium and shake cultured at 30° C. for 16-20 hours. The cells were then diluted to an $A_{600}$ of about 0.01 to 0.1 and maintained in log phase in YPD medium at 30° C. for about 6-8 hours. 100 ml of YPD medium was inoculated with 0.5 ml of the seed culture at an $A_{600}$ of about 0 1 and shake cultured at 30° C. for about 16-20 hours. The culture was then harvested with an $A_{600}$ that was about 0.2 to 0.3 (after approximately 16-20 hours) by centrifugation using a DAMON IEC DPR-6000 centrifuge at 1500 g for 5 minutes.

To prepare spheroplasts, the cells were washed once in 10 ml of sterile water (centrifugation was performed after each wash as described above), once in 10 ml of freshly prepared SED, once in 10 ml of sterile 1M sorbitol, and resuspended in 5 ml of SCE buffer. 5 μl of 4 mg/ml Zymolyase 60,000 (available from Miles Laboratories) was added and the cells incubated at 30° C. for about 30 minutes.

Spheroplast formation was monitored as follows. 100 μl aliquots of cells were added to 900 μl of 5% SDS and 900 μl of 1M sorbitol before or just after the addition of Zymolyase, and at various times during the incubation period. The incubation was stopped at the point where cells would lyse in SDS but not sorbitol. Once formed, spheroplasts were washed once in 10 ml of sterile 1M sorbitol by centrifugation at 1,000 g for 5-10 midutes, washed once in 10 ml of sterile CaS by centrifugation, and resuspended to 0.6 ml in CaS.

For the actual transformation, DNA samples in water or TE buffer were added (up to 20 μl total volume) to 12×75 mm sterile polypropylene tubes. (For small amounts of DNA, maximum transformation occurs using about 1 μl of 5 mg/ml sonicated *E. coli* DNA in each sample.) 100 μl of spheroplasts were added to each DNA sample and incubated at room temperature for about 20 minutes. 1 ml of PEG solution was added to each sample and incubated at room temperature for about 15 minutes. The samples were centrifuged at 1,000 g for 5-10 minutes and the supernatant was discarded. The pellets were resuspended in 150 μl of SOS and incubated at room temperature for 30 minutes. 850 μl of sterile 1M sorbitol was added to each, and the samples were plated as described below.

10 ml of Regeneration Agar was poured per plate at least 30 minutes before transformation samples were ready. 10 ml aliquots of Regeneration Agar were also distributed to tubes in a 45°-50° bath during the period that transformation samples were in SOS. Samples were then added to the tubes, poured onto plates containing the solid bottom agar layer, and incubated at 30° C. for 3-5 days.

Spheroplast quality at various points was determined as follows. 10 μl of sample was removed and diluted 100× by addition to 990 μl of 1M sorbitol. 10 μl of the dilution was removed, and an additional 990 μl aliquot of 1M sorbitol was added. 100 μl of both dilutions were spread-plated on YPD agar medium to determine the concentration of unspheroplasted whole cells remaining in the preparation. 100 μl of each dilution was added to 10ml of Regeneration Agar which had been supplemented with 40 μg/ml of all amino acids required by the host to determine the total regeneratable spheroplasts. Good values for a transformation experiment were 1–3×10⁷ total regenerable spberoplasts/ml and about 1×10³ wbole cells/ml.

EXAMPLE V

Yeast DNA Preparation

The following protocol was used in the preparation of *Pichia pastoris* DNA.

Yeast cells were grown in 100 ml of YNB medium plus 2% dextrose at 30° C. until $A_{600}$ equaled 1–2 and then pelleted using a Damon IEC DPR-6000 centrifuge at 2,000 g for 5 minutes. The pellet was washed once in $dH_2O$, once in SED, once in 1M sorbitol and then resuspended in 5 ml of a solution of 0.1 M Tris-Cl, pH 7.0, and 1M sorbitol. The cells were then mixed with 50–100 μl of a 4 mg/ml solution of Zymolyase 60,000 (Miles Laboratories) and incubated at 30° C. for 1 hour. The resulting spheroplasts were then centrifuged at 1,000 g for 5–10 minutes and suspended in 5 ml Lysis Buffer [0.1% SDS, 10 mM Tris-Cl (pH 7.4), 5 mM EDTA and 50 mM NaCl]. Proteinase K (Boehringer Mannheim) and RNase A (Sigma) were each added to 100 μg/ml and the solution incubated at 37° C. for 30 minutes. DNA was deproteinized by gently mixing the preparation with an equal volume of CI, and the phases were separated by centrifugation at 12,000 g for 20 minutes. The upper (aqueous) phase was drawn off into a fresh tube and extracted with an equal volume of PCI. The phases were separated as before and the top phase placed in a tube containing 2–3 volumes of cold 100% ethanol. The sample was gently mixed and DNA was collected by spooling onto a plastic rod. The DNA was immediately dissolved in 1 mL of TE buffer and dialyzed overnight at 4° C. against 100 volumes TE buffer.

EXAMPLE VI

Isolation of the Full Length PHO1 Gene

To isolate a plasmid containing the entire *Pichia pastoris* PHO1 gene (SEQ ID NO:1), the original *Pichia pastoris* genomic library in MC1061 was hybridized, under the conditions described previously, with the 600 bp BamHI fragment from pLP24. This procedure identified five positive clones. Plasmid DNA was prepared from these clones, digested with BamHI, blotted to nitrocellulose filters, and hybridized with the same 600 bp probe. Each of the five clones had the 2.0 kb BamHI fragment, which contained the *Pichia pastoris* PHO1 gene. One of the clones was chosen for further analysis, and was designated pLP2420.

The 2.0 kb BamHI fragment of pLP2420 was sequenced by standard dideoxy sequencing of restriction enzyme-digested fragments subcloned in M13 (available from New England Biolabs). Analysis of the sequence revealed an open reading frame of 468 amino acids contained entirely within the 2.0 kb BamHI fragment.

EXAMPLE VII

Development of Strains MB102-26:pLp2430T1 and MB102-26:pLP2430-T3

The 2.0 kb BamHI fragment of pLP2420 containing the PHol gene was ligated into the BamHI site of pYM8, a plasmid which contains the *Saccbaromyces cerevisiae* HIS4 gene and pBR322 sequences. [(pYM8 can be prepared as follows: Ten μg of pYA2 (NRRL B-15874) were digested with SphI/ThaI and the 3.4 kb fragment was gel-purified. Ten μg of pBR322 were digested with SphI/NruI and the 3.95 kb fragment was gel-purified. One hundred ng of the 3.95 kb pBR322 fragment were ligated with 250 ng of the 3.4 kb pYA2 fragment under standard conditions. The correct plasmid was identified on the basis of a 3.1 kb XhoI/SpbI fragment, and called pYM8]. The resulting plasmid was designated pLP2430, and was competent to replicate automonously in *Pichia pastoris* by virtue of a fortuitous ARS function (autonomous replication sequence) residing in the *Saccharomyces cerevisiae* HIS4 gene sequence.

GS190:pLP2412 (Pho⁻), a *Pichia pastoris* strain lacking acid phosphatase activity (see Example III) was mated with *Pichia pastoris* strain MD100-20 (his4, Ade⁻). The mating proctocal used was the same as that disclosed in U.S. Pat. No. 4,812,405, which is berein incorporated by reference. Strain MD100-20 was developed as follows: cells of *Pichia pastoris* strain GSI115 (his4) NRRL Y-15851 were mixed with cells of strain GS247 (Ade⁻) under conditions known to promote zygote formation and diploidization (the protocol for this procedure is found in U.S. Pat. No. 4,812,405, which is berein incorporated by reference) and plated on YNB +dextrose plates to select for the prototrophic diploids. The diploid strain was called MD100. MD100 was cultured under conditions known to induce sporulation of *Pichia pastoris* diploids (also as disclosed in U.S. Pat. No. 4,812,405) and the spore progeny cultured onto YNB dextrose+adenine+histidine plates. Individual colonies were tested for the ability to grow in the absence of adenine or bistidine supplements. A strain able to grow without supplemented histidine but unable to grow without supplemented adenine was identified and called MD100-20.

A diploid strain from this cross, MB102 Pho⁺/Pho⁻, HIS4/his4. Ade⁺/Ade⁻) was sporulated (U.S. Pat. No. 4,812,405) to yield haploid progeny. These progeny were screened on LP indicator plates and on YNB dextrose plates, with or without histidine or adenine supplements, to isolate strain MB102-26 (Pho⁻, his4, Ade⁻).

Strain MB102-26 was transformed with plasmid pLP2430 as described in Example IV. His⁺ transformants were selected and screened for acid phophatase expression on LP indicator plates (see Example III). Five transformants were positive for acid phosphatase expression.

Two of these transformants, MB102-26:pLP2430-T1 and MB102-26:pLP2430-T3, were analyzed for the appropriate regulation of acid phosphatase expression. Each strain was grown in HP or LP medium for 24 hours, to an $A^{600}$ of 2.0. Cells from each culture were assayed for acid phosphatase expression (Bostian et al. 1980; *Proc. Natl. Acad. Sci.* 77:4504–4508), in parallel with untransformed HIS4 cells (MB102-28) carrying the Pho⁻phenotype and HIS4 cells (MB102-51) carrying the Pho⁺, wild type phenotype (Table I). The level of induction of the pLP2430 transformants was virtually identical to that of the wild type strain. Therefore, the 2.0 kb BamHI fragment containing the PHO1 gene inserted in pLP2430 contained the entire acid phosphatase coding region as well as the sequences sufficient to confer appropriate phosphate-regulated expression of acid phosphatase.

TABLE I

| Strain | Genotype | Units AP/OD$^{600}$ | | -fold Induction |
|---|---|---|---|---|
| MB102-26: pLP2430-T1 | ade$^-$, HIS4, PHO1 | 707 | 30,244 | 43 |
| MB102-26: pLP2430-T3 | ade$^-$, HIS4, PHO1 | 852 | 28,198 | 33 |
| MB102-51 | ade$^-$, HIS4, PHO1 | 61.4 | 1,975 | 32 |
| MB102-28 | ade$^-$, HIS4, pho1 | 0.02 | 0.03 | 1.5 |

EXAMPLE VIII

Secretion of Invertase

This Example demonstrates that the PHO1 signal sequence (SEQ ID NO:4) functions when operably linked to heterologous genes. The 2.2 kb SmaI - PvuII fragment containing the SUC2 gene of *Saccharomyces cerevisiae* was isolated from pSEYC306 [(Johnson et al., *Cell* 48, 875 (1987)] and cloned into the SmaI site of either pAO810 or pPSV218 (see Examples XI and XII for description of these parent plasmids). This procedure generated plasmids pAPINV1 and pAPINV2, respectively. These employ the *Pichia pastoris* AOX1 promoter to regulate transcription of an open reading frame from the PHO1 signal sequence (SEQ ID NO:4) into the SUC2 structural gene:

```
PHO1 sequence
... GTGTTCGCT linkers sequence from pSEYC306
CGA GAA TCC CCC GGG GAT CCG TCG
ACC TGC AGC CCA GCT TTG SUC2 sequence
ACA AAC GAA ...
```

Ten μg of each plasmid, pAPINV1 or pAPINV2, were digested with BglII and used to transform GS115 as in Example IV. Transformants containing the BglII fragment of pAPINV1, designated GS115:pAPINV1, were selected for histidine prototrophy and screened for the Mut$^-$ phenotype, which denotes proper integration and disruption at the AOX1 locus. The Mut screen was performed by replica plating colonies from glucose-containing media to methanol-containing media and evaluating growth rate on methanol. Slow growth on methanol was indicative of the Mut- phenotype. Transformants with the BglII fragment of pAPINV2, designated GS115:pAPINV2, were also selected for histidine prototrophy but were screened for the Pho1$^-$ phenotype, which denotes proper integration and disruption at the PHO1 locus (see Example III).

Transformants of each class were identified and cultured in YNB+2% glycerol, in parallel with *Pichia pastoris* strains KM71:GS102(Mut$^-$) and GS115:GS102(Mut$^+$) which contain integrated plasmids identical to pAPINV1, except that the SUC2 gene contains its native signal sequence and lacks the PHO1 signal sequence. These two strains are described in EP 256,421. Also cultured in parallel were strains KM71:pPSV216(Mut$^-$) and GS115:pPSV216(Mut$^+$), which contain integrated plasmids identical to pAPINV2, except that SUC2 sequences are lacking.

Each culture was grown in YNB+2% glycerol to an A$^{600}$ of approximately 3.0. An aliquot of each was removed, washed in sterile water, and resuspended in 10 mls of YNB+0.5% MeOH. Mut$^+$ cultures were resuspended at A$^{600}$=0.02, and Mut$^-$ cultures at A$^{600}$=0.2, and grown at 30° C. for 24 hours to approximately A$^{600}$=0.3-0.4. At this time, approximately 1.0 mOD$^{600}$ was assayed for invertase activity. The results are shown in Table II.

TABLE II

| Culture | MUT | Signal Sequence | Secreted Invertase$^a$ | Total Invertase$^b$ | Secretion Efficiency$^c$ |
|---|---|---|---|---|---|
| GS115: pAPINV1 | − | PHO1 | 20.3 | 3.05 | 0.67 |
| KM71: GS102 | − | SUC2 | 12.5 | 18.9 | 0.66 |
| KM71: pPSV216 | − | PHO1$^d$ | 0 | 0 | NA |
| GS115: pAPINV2 | + | PHO1 | 6.1 | 6.7 | 0.91 |
| GS115: GS102 | + | SUC2 | 5.3 | 5.7 | 0.93 |
| GS115: pPSV216 | + | PHO1$^d$ | 0 | 0 | NA |

$^a$secreted invertase - measured as per Goldstein and Lampen*, without Triton, expressed as units of invertase/A$^{600}$ of culture assayed. 1 Unit = 1 μmole of glucose released/minute, at 37° C.
$^b$total invertase - measured in the presence of 0.2% Triton X-100.
$^c$secretion efficiency - secreted invertase/total invertase assayed.
$^d$PHO1 signal present, no SUC2 sequences
*Goldstein and Lampen, Methods in Enzymolology 42:504–511, 1975.

The results clearly show that the PHO1 signal sequence functions as efficiently as the SUC2 signal sequence, to promote invertase secretion from *Pichia pastoris*.

EXAMPLE IX

Secretion of tPA (Tissue Plasminogen Activator)

This Example demonstrates that the PHO1 signal sequence (SEQ ID NO:3) functions when operably linked to heterologous genes.

1. Isolation of tPA-encoding cDNA

The Bowes melanoma tPA-overexpressing cell line, ATCC#CRL9607, was the source of RNA used to construct a cDNA library. This cell line was used by others to clone tPA sequences (Pennica et al., *Nature* 301:214, 1983; Edlund et al., *PNAS* 80:349, 1983; Lemontt et al., *DNA* 4:419,1985). Poly A+RNA was isolated and oligo dt-primed, generally following the procedure in Maniatis (*Molecular Cloning: A Laboratory Manual*; Cold Spring Harbor Laboratory, 1982). The RNA was used to make cDNA using a commercial cDNA cloning kit (available from Amersham), and inserted into the λgt11 cloning vector. λgt11 phage containing inserts were infected into *E. coli* host Y1088, using a commercial packaging mixture (available from Stratagene).

The library was triplicate plated and probed with three different oligonucleotides designed from the published sequence of the human tPA cDNA (Pennica et al., supra). The oligonucleotides corresponded to the 5', middle, and 3' sections of the cDNA and were of the following sequences:

```
3' probe:5' GAC TGG ATT CGT GAC AAC ATG
    CGA CCG TGA 3' middle probe:5' TCA CAG TAC TCC CAC GTC
    AGC CTG CGG TTC 3'

5' probe:5' GAG CCC TCT CTT CAT TGC ATC
    CAT GAT TGC T 3'
```

Five plaqus were identified which hybridized to all three probes. Restriction digests of the inserts of these clones identified them as encoding tPA based on the published restriction patterns (Pennica et al., supra). The clones differed only in the extent of 5' non-coding sequence present. Clones 4 and 5 were picked for further characterization because they contained DNA inserts of 0.8 kb (5' end), 0.47 kb (middle) and 1.3 kb (3' end) upon EcoRI digestion, suggesting the presence of full-length t-PA coding sequences. The BglII fragment from clone 4 was subcloned into BamHI-cut pUC18, and the ligation was transformed into E. coli MC1061 cells. Positive transformants were identified by EcoRI digestion. A clone carrying the insert in the sense orientation was identified by a PstI restriction pattern of 420bp, 624 bp, 760bp, and 2.7kb fragments and was called pUC18#3. A clone carrying the insert in the antisense orientation was identified by a PstI restriction pattern of 420 bp, 624 bp, and 3.46 kb, and was called pUC18#2. The insert encodes from two nucleotides before the first amino acid of mature tPA through 1972 nucleotides of 3' noncoding sequence.

2. Construction of vector pT37 (PHO1ss-tPA-pUC)

The tPA insert from pUC18#2 was cloned into the Pichia pastoris expression plasmid pAO810. Plasmid pAO810 is comprised of the Pichia pastoris AOX1 promoter, the Pichia pastoris PHO1 signal sequence, the AOX1 transcription terminator, the Pichia pastoris HIS4 gene for selection, an f1 origin of replication, and sequences necessary for replication and selection in bacteria. The construction of pAO810 is described in Example XI.

2 μg of the 1600 bp SalI/SmaI fragment of pUC18#2, previously purified on a 1% agarose gel, encoding the 5'-portion of tPA, was ligated to 300 ng of XhoI/SmaI-digested pAO810. The legation reaction was transformed into E. coli MC1061 cells and ampR colonies were selected. Positives were identified by a pattern of 420 bp, 620 bp, 2kb, and 6.3 kb fragments upon digestion with PstI. The resulting vector was called pT1. Site-directed mutagenesis was performed, following standard procedures for f1 origin of replication vectors, to delete the two extra nucleotides 5' to the mature tPA coding sequence. The mutagenizing oligonucleotide was of sequence:

5' CAA TCT GTC TTC GCT TCT TAC CAA
      GTG ATC 3'

The correct plasmid was identified by screening SalI/XbaI-digested mini-preps. The original vector pT1 had a restriction pattern of 1.2, 2.3, and 6.6 kb. The correctly mutagenized plasmid had a pattern of 1.2 and 9.8 kb and was called pT2-3.

50 μg of pUC18#3 were digested with SmaI/Sau3A. The three bands between 72 and 118 bp (75, 90, 110 bp) encoding the 3' portion of tPA were purified on an 8% polyacrylamide gel and were ligated to 0.5 μg of SmaI/BamHI-cut plasmid pT2-3. The ligation was transformed into E. coli MC1061 cells and ampr colonies were selected. Positives were identified by PvuII/ApaI-digested mini-preps. The correct plasmid exhibited a 421 bp fragment (incorrect showed a 225 bp fragment). Correct vector was called pT37. The 5' mutagenesis was shown to be of the correct sequence, however, sequencing revealed that the plasmid contained pUC18 sequences following the end of the tPA 3' noncoding sequence; plasmid pT37 was shown to have the Sau3A fragment from pUC18, position 1894–2004, immediately following the t-PA sequence.

10 μg of plasmid pT37 was digested with StuI and used to transform Pichia pastoris strain KM71 (aox1, his4). Transformants were selected for histidine prototrophy. A transformant, KM71:pT37 was cultivated in YNB+2% glycerol, in parallel with strain KM71:pT7, which contained a plasmid (pT7) almost identical to pT37 except that the PHO1 signal sequence was replaced with the native human tPA signal sequence and the pUC18 sequences at the 3' end were removed. A description of pT7 is provided hereinbelow. 50 ml cultures of each strain growing in YNB+2% glycerol were seeded into one liter fermentors and grown either in continuous mode or fed-batch mode. The results of this experiment are shown in Table III.

TABLE III

| | | | | *tPA μg/L | | | |
|---|---|---|---|---|---|---|---|
| Run# | Strain | Signal | Mode | Internal | External | Total | Efficiency** |
| 1 | KM71:pT7 | tPA | continuous | 255 | 60 | 315 | .19 |
| 2 | KM71:pT7 | tPA | fed batch | 651 | 30 | 681 | .04 |
| 3 | KM71:pT37 | PH01 | continuous | 840 | 420 | 1260 | .33 |
| 4 | KM71:pT37 | PH01 | fed batch | 1856 | 1200 | 3056 | .39 |

*tPA assayed by ELISA using human tPA as standard
**efficiency of tPA secretion = external tPA/total tPA produced The results of this experiment show that regardless of the mode of fermentation the PHO1 signal sequence (SEQ ID NO:4) was more efficient at promoting tPA secretion in Pichia pastoris than was the native signal sequence.

In addition, micro-Edman degradation analysis confirmed that the N-terminal amino acid sequence of the recombinant, secreted tPA from strain KM71:pT3, using the PHOL signal sequence (SEQ ID NO:4) was identical to the native tPA purified from a cultured human tissue (melanoma) source.

3. Construction of pT7 (tPAss-tPA-no pUC)

5 μg of the approximately 100 bp SmaI/Sau3A fragment from pUC18#3 was ligated to 500 ng of SmaI/BamHI-cut pT1. The ligation reaction was transformed into E. coli MC1061 cells and ampR colonies were selected. Positives were identified by the presence of a 360 bp band, rather than a 260 bp band, upon digestion with ApaI/PvuII. The modified 3' end was sequenced and shown to be of the correct sequence with no extra pUC18 sequences. This plasmid was called pT49.

Oligonucleotides encoding the authentic t-PA signal sequence were added to the XbaI site of plasmid pT49, and then two mutageneses were performed to 1) delete the extra 8 nucleotides of sequence remaining between the t-PA signal sequence and the sequence coding for mature t-PA, and 2) delete the PflO1 signal sequence. These manipulations were accomplished as follows.

An oligonucleotide of the following sequence was synthesized (109 nucleotides):

5' CTA GAT GGA TGC AAT GAA GAG AGG GCT CTG CTG TGT GCT GCT GCT    (SEQ ID NO:9)

GTG TGG AGC AGT CTT CGT TTC GCC CAG CCA GGA AAT CCA TGC CCG ATT

CAG AAG AGG AGC CAG A3'

The complementary oligonucleotide needed for the second strand was synthesized as three oligonucleotides, of 33, 37, and 39 nucleotides in length, respectively, which were of the following sequences:

5' CTG GCT GGG CGA AAC GAA GAC TGC TCC ACA CAG 3'    (SEQ ID NO:10)

5' CTA GTC TGG CTC CTC TTC TGA ATC GGG CAT GGA TTT C 3'    (SEQ ID NO:11)

5' CAG CAG CAC ACA GCA GAG CCC TCT CTT CAT TGC ATC CAT 3'    (SEQ ID NO:12)

The full length oligonucleotide and the three complementing oligoriucleotides were kinased and then annealed together by heating in a boiling water bath for 3 min, and then slowly cooled to room temperature. Annealed oligonucleotide was separated and isolated from a 5% polyacrylamide gel.

200 ng of partially XbaI-linearized pT49 was ligated to 1 μg of the annealed doable-stranded oligonucleotide. The ligation reaction was transformed into E. coli MC1061 cells and ampR colonies were selected. Clones containing the correctly altered plasmid were identified by an additional 700 bp band upon digestion with AsuII. A correct plasmid was called pT544.

The first mutagenesis was accomplished by standard fl-based site-directed mutagenesis using pT544 DNA (5 μg) and an oligonucleotide (1 μg) of the following sequence:

5' GA TTC AGA GGA GCC AGA TCT TAC CAA GTG ATC TGC AG 3'    (SEQ ID NO:13)

The correct plasmid was screened for by BglII digestion. The correct restriction pattern (1.1, 2.8 and 5.3 kb) was indicative of correct plasmid, which was called pT64. (Incorrect plasmid showed a pattern of 2.8 and 6.3 kb bands.)

The second round of mutagenesis was performed with plasmid pT64 to delete the PHOL signal sequence. An oligonucleotide of the following sequence was used:

5' ACT AAT TAT TCG AAA CGA TGG ATG CAA TGA AGA GAG G 3'    (SEQ ID NO:14)

3 μg of pT64 and 0.4 μg of the oligonucleotide above were used in the mutagenesis. Mini-preps were screened by digestion with BglII. The correct plasmid was identified by three DNA fragments of 1, 2.8, and 5.3 kb in size (incorrect plasmid showed a smallest band of 1.1 kb instead of 1 kb). The mutagenesis was confirmed by sequencing, and the correct plasmid was called pT7.

EXAMPLE X

Construction of pAPB101: PHO1 promoter-lacZ expression plasmid

This Example demonstrates that the PHO1 promoter (or 5' regulatory region) (SEQ ID NO:3) functions when operably linked to heterologous genes. 1. μg of the lacZ-containing plasmid pSAOH5 (NRRL B-15862) was digested with EcoRI and BAMHI, and the 10.1 kb vector fragment was isolated from a 0.8% agarose gel.

5 pg of pLP2420 were digested with EcoRI and BCII and the 1.6 kb fragment, containing 375 bp of pBR322 DNA, ~1075 bp of the PHO1 5' flanking DNA including the PHO1 promoter (SEQ ID NO:3), and 123 bp of PHO1 coding sequence was isolated from a 1% agarose gel. 100 ng of the EcoRI-BamHI fragment of pSAOH5 and 60 ng of the 1.6 kb EcoRI-BelI fragment of pLP2420 were ligated in a 20 μl mixture of ligase buffer with 1. mM ATP and 1U of T4 DNA ligase (available from Boehringer Mannheim). The legation mixture was transformed into E. coli JM103, and the transformed cells were plated onto LB Amp plates which contained 40 μg/ml X-gal. Blue-colored colonies were chosen, grown in LB Amp and plasmid DNA was isolated. The DNA was digested with EcoRI and SmaI and the correct plasmid was identified by the release of a 1450 bp fragment. The correct plasmid was called pAPB101. An expression cassette comprised of the E. coli lacZ gene placed under the regulation of the Pichia pastoris PHO1 promoter element (SEQ ID NO:3) was contained in pAPB101.

10 μg of uncut pAPB101 were transformed into GS115 spberoplasts and histidine prototrophs were selected. 12 His+ colonies were chosen, the strains grown in liquid high phosphate (HP) and LP media, and assayed for β-galactosidase activity. Positive transformant strains were identified on the basis of β-galactosidase expression after growth in LP media and a lack of β-galactosidase after growth in HP media. β-galactosidase was assayed as per J.H. Miller, *Experiments in Molecular Genetics*, Cold Spring Harbor Labs, Cold Spring Harbor, NY 1972. Blue colonies appeared on the LP-X-gal plates and white colonies appeared on the HP-X-gal plates.

EXAMPLE XI

The following plasmids were constructed for use in other Examples in this application.

1. Construction of Plasmid pAO810

M13mp19ΔRI was constructed by digesting 1 μg of M13mp19 with EcoRI, filling in with Klenow and ligating the filled-in fragment to itself; the ligation was used to transform E. coli JM103 cells, and correct phage was identified by isolating DNA and digesting it with EcoRI. Correct phage was not cut by EcoRI and was called M13mp19ΔRI. Plasmid pAO804 (the construction of which is described in WO89/04320, which is herein incorporated by reference, was digested with SstI and EcoRV and the approximately 1.2 kb fragment was isolated from an 0.8% agarose gel. (All fragments in this construction were isolated from 0.8-1.0% agarose gels.) 100 ng of fragment were ligated to 500 ng of SstI- and SmaI-digested M13mp19ΔRI. The ligation was used to transform E. coli JM103 cells, and correct phage was identified by isolating DNA and digesting it with SstI and PvuII. Correct phage was identified by the presence of a 950 bp fragment, and was called pPSV101.

One picomole of pPSV101 was subjected to in vitro oligonucleotide-directed, site-specific mutagenesis using 20 pmol of an oligonucleotide of the following sequence:

5' CGA GGA ATT CCC CGG GAT CCT TAG ACA T 3'(SEQ. ID. NO:15)

The reaction mixture was used to transform E. coli JM103 cells. Correct phage were identified by digestion of mini-prep DNA with BglII and BamHI, revealing the presence of 1.4 kb and 0.5 kb DNA fragments. The correct phage was called pPSV102.

Plasmid pPSV102 was digested with EcoRI and 500 ng of the 8.5 kb fragment were ligated to 50 ng of the following double-stranded synthetic DNA fragment coding for the Pichia pastoris PHO1 signal sequence (SEQ ID NO:4) using the following optimized Pichia codons:

2. Creation pAO807 a. Preparation of fl-ori DNA fl bacteriophage DNA (50 ug) was digested with 50 units of RsaI and DraI (according to manufacturer's directions) to release the ~458 bp DNA fragment containing the fl origin of replication (ori). The digestion mixture was extracted with an equal volume of PCI followed by extracting the aqueous layer with an equal volume of CI and finally the DNA in the aqueous phase was precipitated by adjusting the NaCl concentration to 0.2M and adding 2.5 volumes of absolute ethanol. The mixture was allowed to stand on ice (4° C.) for 10 minutes and the DNA precipitate was collected by centrifugation for 30 minutes at 10,000 xg in a microfuge at 4° C.

The DNA pellet was washed 2 times with 70% aqueous ethanol. The washed pellet was vacuum dried and dissolved in 25 ul of TE buffer. This DNA was electrophoresed on 1.5% agarose gel and the gel portion containing the ~458 bp fl-ori fragment was excised out and the DNA in the gel was electroeluted onto DE81 (Whatman) paper and eluted from the paper in 1M NaCl. The DNA solution was precipitated as detailed above and the DNA precipitate was dissolved in 25 ul of TE buffer (fl-ori fragment).

b. Cloning of fl-ori into DraI sites of pBR322:

PBR322 (2 ug) was partially digested with 2 units DraI (according to the manufacturer's instructions).

```
5'-AATTC ATG TTC TCT CCA ATT TTG TCC TTG GAA ATT ATT TTA GCT TTG GCT ACT       (SEQ ID NO:16)

3'-G TAC AAG AGA GGT TAA AAC AGG AAC CTT TAA TAA AAT CGA AAC CGA TGA        (SEQ ID NO:17)

TTG CAA TCT GTC TTC GCT CGA G-3'                                            (SEQ ID NO:8)

AAC GTT AGA CAG AAG CGA GCT C TTAA-5'                                       (SEQ ID NO:19)
```

The ligation mixture was transformed into E. coli CJ236 cells and the correct phage DNA was identified by plaque hybridization with one coding strand of the yeast signal sequence, which bad been labeled with $^{32}P$, and by digestion of the hybridizing DNA with SstI and BamHI, revealing a 700 bp fragment. The plasmid was called pPSV103.

One picomole of pPSV103 was mutagenized in vitro with 20 pmoles of an oligonucleotide of the sequence:

5' CTAA TTA TTC GAA ACG ATG TTC TCT CCA ATT 3'(SEQ ID NO:20)

Correct phage DNA was identified by plaque bybridization with the same oligonucleotide used above. The correct plasmid was called pPSV104.

Plasmid pAO810 was prepared by digesting 10 μg of pPSV104 with HindIII, and isolating the 400 bp DNA fragment from a 1.2% agarose gel. 50 ng of this fragment were ligated with 250 ng of the 7.9 kb HindIII digestion product of pAO807 (the preparation of which is described hereinbelow) as isolated from a 0.8% agarose gel. The ligation was transformed into E. coli MC1061 cells and ampr colonies were selected. Correct plasmid was identified by the presence of a 450 bp band upon digestion with BamHI and EcoRV, and was called pAO810.

The reaction was terminated by PCI extraction followed by precipitation of DNA as detailed in step a above. The DNA pellet was dissolved in 20 ul of TE buffer. About 100 ng of this DNA was ligated with 100 ng of fl-ori fragment (step a) in 20 ul of ligation buffer by incubating at 14° C. for overnight with 1 unit of T4 DNA ligase. The ligation was terminated by heating to 70° C. for 10 minutes and then used to transform E. coli strain JM103 to obtain pBRfl-ori which contains fl-ori cloned into the DraI sites (nucleotide positions 3232 and 3251) of pBR322.

c. Creation of pAO807:

pBRfl-ori (10 ug) was digested for 4 hours at 37° C. with 10 units each of PstI and NdeI. The digested DNA was PCI extracted, precipitated and dissolved in 25 ul of TE buffer as detailed in step 1 above. This material was electrophoresed on a 1.2% agarose gel and the NdeI - PstI fragment (approximately 0.8 kb) containing the fl-ori was isolated and dissolved in 20 ul of TE buffer as detailed in step a above. About 100 ng of this DNA was mixed with 100 ng of pAO804 that had been digested with PstI and NdeI and phosphatase-treated. A description of pAO804 is provided in WO89/04320. This mixture was ligated in 20 ul of ligation buffer by incubating for overnight at 14° C. with 1 unit of T4 DNA ligase. The ligation reaction was terminated by heating at 70° C. for 10 minutes. This DNA was used to transform E. coli strain JM103 to obtain pAO807.

Example XII

Construction of pPSV218

200 ng of the 1.6 kb EcoRI/BclI fragment of pLP2420, 100 ng of the 0.8 kb BglII/HindIII fragment of pPG2.5 (see description below), and 100 ng of the 2.6 kb EcoRI/HindIII fragment of pUC8 (New England Biolabs, Inc.) were ligated in a three-part ligation in a 20 µl volume of ligation buffer, 1 mm ATP, 1U T4 ligase and transformed into *E. coli* strain MC1061 for Amp resistance. [Plasmid pPG2.5 is the 2.5 kb EcoRI-SalI fragment of pPG4.0 (NRRL B-15868) placed in pBR322, which contains the alcohol oxidase promoter.] Resistant clones were analyzed for plasmids which contained a 2.4 kb EcoRI+HindIII fragment; the correct plasmid was called pPSV201. 50 ng of pPSV201 were digested with BamHI, dephospborylated, and ligated with a 50-fold molar excess of an oligonucleotide with the following sequence:

5'-GATCAGATCT-3' which converts the BamHI site to a BglII site. Positive clones were identified on this basis and the plasmid was called pPSV203. 10 ng of pPSV203 were partially digested with a limiting amount of HindIII and blunt-ended with Klenow. Linear full length plasmid fragments were gel-purified and self-ligated in a 100 µl volume. Correct clones were identified on the basis of plasmid DNA containing a 1350 bp BglII/HindIII fragment and correct plasmids were called pPSV210.

60 ng of the 500 bp BglII-BamHI fragment of pLP2420 were ligated with 100 ng of BamHI-digested pUC8. Correct plasmids were identified on the basis of a 422 bp NcoI-BamHI fragment; the resulting plasmid was called pPSV202. 50 ng of pPSV202 were digested with BamHI, dephosphorylated, and ligated with a 50-fold molar excess of an oligonucleotide with the sequence:

5'-GATCAGATCT-3' which converted the BamHI site to a BglII site. The correct plasmid was identified on the basis of a 422 bp NcoI/BglII fragment, and called pPSV204.

10 µg of pPSV210 were digested with BglII and SacI, and the 700 bp fragment gel-purified. 25 ng of this fragment were ligated to 100 ng of the gel-purified, 8200 bp BglII/SacI fragment of pAO810. Correct plasmids were identified by the presence of a 700 bp BglII/SacI fragment and were called pPSV212. 10 µg of pPSV212 were digested with SphI, blunt-ended with T4 DNA polymerase (as per Maniatis et al.), partially digested with BglII, and the 8000 bp fragment was gel purified. 10 µg of pPSV204 were digested with NcoI, blunt-ended with Klenow, digested with BglII, and the 440 bp fragment was gel-purified. 100 ng of the above-described 8 kb fragment from pPSV212 were ligated to 15 ng of the 440 bp fragment from pPSV204. The correct plasmid was identified on the basis of a 5500 bp BglII fragment and was called pPSV218.

The Examples have been provided merely to illustrate the practice of the present invention and should not be read so as to limit the scope of the invention or the appended claims in any way. Reasonable variations and modifications, not departing from the essence and spirit of the invention, are contemplated to be within the scope of patent protection desired and sought.

---

That which is claimed is:

1. An isolated DNA fragment consisting essentially of the *P. pastoris* acid phosphatase gene.

2. A DNA according to claim 1 wherein said DNA fragment has the restriction map shown in FIG. 1.

3. A DNA according to claim 1 wherein said DNA fragment comprises the nucleotide sequence represented by SEQ. ID NO: 1.

4. An isolated DNA fragment consisting essentially of the *P. pastoris* acid phosphatase 5' regulatory region.

5. A DNA according to claim 4 which comprises the DNA sequence corresponding to nucleotides 1-399 of SEQ. ID NO: 1.

6. An isolated DNA consisting essentially of a DNA segment which encodes the 22-amino acid residue acid phosphatase signal sequence represented in SEQ. ID NO: 5.

7. A DNA according to claim 6 wherein the nucleotide sequence which encodes the signal sequence is the nucleotide sequence represented in SEQ. ID NO: 4.

8. An isolated DNA comprising a DNA segment which encodes a 22-amino acid residue P. pastoris acid phosphatase signal sequence operatively linked to a heterologous DNA sequence which encodes at least one polypeptide.

9. A DNA according to claim 8 wherein said heterologous DNA segment encodes tissue plasminogen activator.

10. An isolated DNA fragment consisting essentially of the P. pastoris acid phosphatase structural gene.

11. A DNA according to claim 10 which comprises a nucleotide sequence which encodes the 446-amino acid sequence represented by SEQ ID NO: 7.

12. A DNA according to claim 11 which comprises the nucleotide sequence represented by SEQ ID NO: 6.

13. A plasmid DNA containing an expression cassette, said expression cassette comprising: (1) a regulatory region of a first P. pastoris gene which is the P. pastoris acid phosphatase gene, (2) a transcribable DNA segment which encodes a heterologous polypeptide, and (3) a transcription terminator of a second P. pastoris gene, said segments being operably linked for expression of the polypeptide encoded by said heterologous DNA segment.

14. A DNA according to claim 13 wherein the first P. pastoris gene and the second P. pastoris gene are the P. pastoris acid phosphatase gene.

15. A DNA according to claim 13 further comprising a selectable marker gene.

16. A P. pastoris cell comprising a DNA containing an expression cassette, said expression cassette comprising: (1) a regulatory region of a first P. pastoris gene, (2) a transcribable DNA segment which encodes a heterologous polypeptide, and (3) a transcription terminator of a second P. pastoris gene, said segments being operably linked for expression of the peptide encoded by said heterologous DNA segment, provided that at least one of the first P. pastoris gene and the second P. pastoris gene is the P. pastoris acid phosphatase gene.

17. A P. pastoris cell according to claim 16 wherein the first P. pastoris gene and the second P. pastoris gene are the P. pastoris acid phosphatase gene.

18. A P. pastoris cell according to claim 16 further comprising a selectable marker gene.

19. A method for producing and secreting a heterologous polypeptide into culture medium comprising growing P. pastoris cells transformed with a DNA comprising an expression cassette for the expression of a transcribable DNA segment comprising the P. pastoris acid phosphatase signal sequence operatively linked to a polypeptide-encoding segment under conditions allowing the expression and secretion of said polypeptide into the culture medium.

20. A method according to claim 19 wherein the heterologous polypeptide is tissue plasminogen activator.

21. A method for expressing a heterologous peptide comprising growing a P. pastoris cell transformed with a DNA comprising an expression cassette, said expression cassette comprising: (1) a regulatory region of a first P. pastoris gene, (2) a transcribable DNA segment which encodes a heterologous polypeptide, and (3) a transcription terminator of a second P. pastoris gene, said segments being operably linked for expression of the peptide encoded by said heterologous DNA segment, provided that at least one of the first P. pastoris gene and the second P. pastoris gene is the P. pastoris acid phosphatase gene.

22. A method according to claim 21 wherein the first and the second P. pastoris genes are the acid phosphatase gene.

23. A method according to claim 21 wherein the DNA comprising said expression cassette further comprises a selectable marker gene.

24. A method according to claim 23 wherein said transforming DNA comprises a first insertable DNA segment having a sequence of at least about 200 nucleotides corresponding to a first portion of SEQ ID NO: 1 and a second insertable DNA segment having a sequence of at least about 200 nucleotides corresponding to a second portion of SEQ ID NO: 1, said first insertable DNA segment being positioned 5' to the polypeptide encoding heterologous DNA segment and the second insertable DNA segment being positioned 3' to the polypeptide encoding heterologous DNA segment such that the DNA is capable of being integrated into the genome of said P. pastoris cell at the acid phosphatase locus.

25. A method according to claim 23 wherein the heterologous polypeptide is tissue plasminogen activator.

26. A method according to claim 24 wherein the heterologous polypeptide is tissue plasminogen activator.

27. A method for identifying transformed P. pastoris cells which have integrated at least one expression cassette into their genome at the acid phosphatase locus, comprising growing the cells on a medium comprising an acid phosphatase indicator, under conditions allowing for expression of acid phosphatase activity for an amount of time sufficient to distinguish cells producing acid phosphatase activity from cells lacking acid phosphatase activity, and determining the colonies which lack acid phosphatase activity.

28. A plasmid DNA containing an expression cassette, said expression cassette comprising: (1) a regulatory region of a first P. pastoris gene, (2) a DNA segment which encodes the P. pastoris acid phosphatase signal sequence, (3), a DNA segment which encodes a heterologous polypeptide, and (4) a transcription terminator of a second P. pastoris gene, said DNA segments being operably associated with one another for transcription of the sequences encoding said polypeptide having said signal sequence.

29. A DNA according to claim 28 further comprising a selectable marker gene.

30. A DNA according to claim 29 wherein both the first and the second P. pastoris gene are the P. pastoris acid phosphatase gene.

31. A DNA according to claim 30 wherein said polypeptide-encoding segment encodes tissue plasminogen activator.

32. A DNA according to claim 29 wherein both the first and the second P. pastoris gene are the P. pastoris AOX1 gene.

33. A DNA according to claim 32 wherein said polypeptide-encoding segment encodes tissue plasminogen activator.

34. A DNA which is Pichia expression vector pT37.

35. A DNA according to claim 13 which further comprises: a first insertable DNA segment having a sequence of at least about 200 nucleotides corresponding to a first portion of the P. pastoris acid phosphatase gene and a second insertable DNA segment having a sequence of at least about 200 nucleotides corresponding to a second portion of the P. pastoris acid phosphatase gene, said second insertable DNA segment being downstream with respect to the direction of transcription from the first insertable DNA segment, wherein said expression cassette is capable of integrating into the acid phosphatase locus of a P. pastoris cell and producing said heterologous polypeptide, provided that where the first insertable DNA segment does not comprise a regulatory region, the DNA further comprises a regulatory region downstream from the first insertable DNA segment and operably linked to the polypeptide encoding DNA segment, and where the second insertable DNA segment does not comprise a terminator region, the DNA further comprises a terminator region upstream from the second insertable DNA segment and operably linked to the polypeptide encoding DNA segment.

36. A DNA according to claim 35 wherein the first insertable DNA segment comprises the regulatory region of the P. pastoris acid phosphatase gene and the second insertable DNA segment comprises the terminator region of the P. pastoris acid phosphatase gene.

37. A P. pastoris cell comprising a DNA containing an expression cassette, said expression cassette comprising:

(1) a regulatory region of a first P. pastoris gene, (2) a DNA segment which encodes the P. pastoris acid phosphatase signal sequence, (3) a DNA segment which encodes a heterologous polypeptide, and (4) a transcription terminator of a second P. pastoris gene, said DNA segments being operably associated with one another for transcription of the sequences encoding said polypeptide having said signal sequence.

38. A P. pastoris cell according to claim 37, said expression cassette further comprising a selectable marker gene.

39. A P. pastoris cell according to claim 38 wherein both the first and the second P. pastoris gene are the P. pastoris acid phosphatase gene.

40. A P. pastoris cell according to claim 39 wherein said polypeptide-encoding segment encodes tissue plasminogen activator.

41. A P. pastoris cell according to claim 38 wherein both the first and the second P. pastoris gene are the P. pastoris AOX1 gene.

42. A P. pastoris cell according to claim 44 further comprising a selectable marker gene.

43. A P. pastoris cell according to claim 42 wherein said polypeptide-encoding segment encodes tissue plasminogen activator.

44. A P. pastoris cell according to claim 37 which comprises Pichia expression vector pT37.

* * * * *